(12) United States Patent
Khoshnan et al.

(10) Patent No.: US 7,375,194 B2
(45) Date of Patent: May 20, 2008

(54) ANTIBODIES THAT BIND TO AN EPITOPE ON THE HUNTINGTON'S DISEASE PROTEIN

(75) Inventors: Ali Khoshnan, South Pasadena, CA (US); Jan Ko, Arcadia, CA (US); Paul H. Patterson, Altadena, CA (US)

(73) Assignee: California Institute of Technology, Pasadena, CA (US)

( * ) Notice: Subject to any disclaimer, the term of this patent is extended or adjusted under 35 U.S.C. 154(b) by 525 days.

(21) Appl. No.: 10/354,246

(22) Filed: Jan. 28, 2003

(65) Prior Publication Data

US 2003/0232052 A1 Dec. 18, 2003

Related U.S. Application Data

(60) Provisional application No. 60/353,032, filed on Jan. 28, 2002.

(51) Int. Cl.
*C12P 21/08* (2006.01)
*C07H 21/04* (2006.01)
*C07K 16/18* (2006.01)
*A61K 39/395* (2006.01)

(52) U.S. Cl. ............... 530/387.3; 424/139.1; 530/387.9; 530/388.2; 536/23.53

(58) Field of Classification Search ............. 530/387.3, 530/387.9, 388.2, 389.1; 424/139.1; 536/23.53
See application file for complete search history.

(56) References Cited

U.S. PATENT DOCUMENTS 5,693,757 A 12/1997 MacDonald et al.
6,291,652 B1 9/2001 Finkbeiner

FOREIGN PATENT DOCUMENTS

WO WO 02/29408 4/2002

OTHER PUBLICATIONS

Campbell, 1984. Monoclonal Antibody Technology, Elsevier, Amsterdam. pp. 1-4 and 29.*
Harlow et al., 1988. Antibodies. A Laboratory Manual, Cold Spring Harbor Laboratory, Cold Spring Harbor. pp. 72-77.*
Maurer et al., 1980. Proteins and polypeptides as antigens. Meth. Enzymology 70: 49-70.*
Mozes et al., 1973. Genetic control of immune response in mice to derivatives of multichain polyproline differeing in the optical configuration of component amino acids. Eur. J. Immunol. 3: 1-6.*
Uhlig et al., 1989. Monoclonal autoantibodies derived form multiple sclerosis patients and control persons and their reactivities with antigens of the central nervous system. Autoimmunity 5: 87-99.*
Dillner et al., 1985. Antibodies against synthetic peptides react with the second Epstein-Barr virus-associated nuclear antigen. EMBO Journal 4: 1813-1818.*
Linde et al., 1990. Evaluation of enzyme-linked immunosorbent assays with two synthetic peptides of Epstein-Barr virus for diagnosis of infectious mononucleosis. J. Infectious Diseases 161: 903-909.*
Bengtsson et al., 1996. Selective antibody reactivity with peptides from human endogenous retroviruses and nonviral poly(amino acids) in patients with systemic lupus erythematosus. Arthritis Rheumatism 39: 1654-1663.*
Reddy et al. Trends Neurosci. 22:248-255 (1999).
Zoghbi et al. Annu. Rev. Neurosci. 23:217-247 (2000).
Tobin et al. Trends Cell Biol. 10:531-536 (2000).
Ross et al. Neuron 19:1147-1150 (1997).
Wanker et al. Biol. Chem. 937-942 (2000).
Ferrigno et al. Neuron 26:9-12 (2000).
Khoshnan et al. Proc. Natl. Acad. Sci. USA 99:1002-1007 (2002).
Ko et al. Brain Res. Bulletin 56:319-329 (2001).
Trottier et al. Nature Genetics 10:104-110 (1995).
Trottier et al. Nature 378:403-406 (1995).
Collaborative Research Group Cell 72:971-983 (1995).
Li et al. Nature 378:398-402 (1995).
Lin et al. Hum. Mol. Genet. 3:85-92 (1994).
Rubinsztein et al. Nature Genet. 5:214-215 (1993).
Onodera et al. FEBS Lett. 399:135-139 (1996).
Wheeler et al. Hum. Mol. Genet. 9:503-513 (2000).
Menalled et al. Exp. Neurol. 162:328-342 (2000).
Mende-Mueller et al. J. Neursci. 21:1830-1837 (2001).

* cited by examiner

*Primary Examiner*—Long V. Le
*Assistant Examiner*—James L. Grun
(74) *Attorney, Agent, or Firm*—Knobbe Martens Olson & Bear LLP

(57) ABSTRACT

The present invention relates generally to the generation and characterization of anti-huntingtin antibodies binding an epitope on the Huntington's disease protein. The invention further relates to the use of such anti-huntingtin antibodies in the diagnosis and treatment of Huntington's disease.

1 Claim, 18 Drawing Sheets

Epitope mapping of MW mAbs

MATLEKLMKAFESLKSFQQQQQQQQQQQQQQQQQQQQPPPPPPPPQLPQPPPQAQPLLPQPQPPPPPPPPPGPAVAEEPLHRPK  SEQ ID NO: 1

MW1－4    MW7    MW7    MW8

FIG. 2

ANTIBODIES THAT BIND TO AN EPITOPE ON THE HUNTINGTON'S DISEASE PROTEIN

RELATED APPLICATIONS

This application claims priority under 35 U.S.C. §119(e) from U.S. provisional application No. 60/353,032, filed on Jan. 28, 2002 and entitled "COMPOSITIONS AND METHODS FOR THE TREATMENT OF HUNTINGTON'S DISEASE."

BACKGROUND OF THE INVENTION

1. Field of the Invention

The present invention relates generally to antibodies to Huntington's disease protein as well as methods and means for making and using such antibodies.

2. Description of the Related Art

Huntington's disease (HD) is a fatal autosomal dominant neurodegenerative disorder that is caused by the extension of a polyglutamine (polyQ) tract in exon 1 the protein huntingtin (Htt) to a length of greater than 40 units (Reddy et al. Trends Neurosci. 22:248-255 (1999)). The huntingtin gene is known and the subject of U.S. Pat. No. 5,693,757. Mutant Htt with greater than 40 CAG repeats gains a toxic function and induces death in subpopulations of neurons in the striatum and cortex (Zoghbi et al. Annu. Rev. Neurosci. 23:217-247 (2000); Tobin et al. Trends Cell Biol. 10:531-536 (2000)). Neuronal death in HD has been attributed not only to polyQ toxicity, but also to activation of caspases, interference with transcriptional machinery, and sequestration/inactivation of wild-type Htt and other important cellular factors.

A hallmark of HD and other polyQ diseases is the formation of insoluble protein aggregates in affected neurons (Ross Neuron 19:1147-1150 (1997); Wanker Biol. Chem. 937-942 (2000). Immunohistochemistry and subcellular fractionation indicate that Htt is normally located in the cytoplasm while the mutant form of Htt is also found in aggregates in the nucleus (Ferrigno et al. Neuron 26:9-12 (2000)). A major component of the aggregates in HD is the N terminus exon 1 of mutant Htt. As normal huntingtin protein is localized in the cytoplasm and mutant huntingtin protein is found in aggregates, also known as and referred to as inclusions, in the nucleus (Ferrigno et al., Neuron, 26:9-12 (2000)), translocation of mutant huntingtin protein to the nucleus is believed to be important in the pathogenesis of HD.

Because there is no current treatment available for this disease, there is a clear need for new treatments for Huntington's disease. Molecules that block the toxic effects of Htt itself or the lethal consequences of its binding to other proteins have good potential for therapeutic use. Thus, antibodies may serve as treatments for Huntington's disease. An antibody termed 1C2 is described in WO 97/17445. Finkbeiner (U.S. Pat. No. 6,291,652) provides antibodies specific for proteins having polyglutamine expansions. In particular, Finkbeiner provides antibodies having a higher affinity than an antibody identified as 1C2.

SUMMARY OF THE INVENTION

In one aspect, the invention involves antibodies, specifically monoclonal antibodies including antibody fragments, such as single-chain variant fragments, and mimetics thereof (including intrabodies), to the huntingtin protein. Preferred biological activities of the antibodies include the capability of preventing cell death or apoptosis, preventing mutant huntingtin protein aggregation and the regulating the toxic effects of mutant huntingtin protein that are associated with neurodegenerative disease. In one embodiment, the antibodies bind specifically to an epitope within a polyproline region of the huntingtin protein comprising greater than 5 consecutive proline residues and are capable of inhibiting aggregation of huntingtin protein. In another embodiment, the antibodies bind specifically to an epitope within the polyglutamine region of the huntingtin protein comprising greater than 6 consecutive glutamine residues and are capable of stimulating aggregation of huntingtin protein. In another embodiment, the antibodies specifically interact with an amino acid epitope within the carboxy terminus of the protein encoded by exon 1 of the huntingtin protein, said carboxy terminus comprising the amino acid sequence of SEQ ID NO: 2. In another embodiment, the antibodies are in association with a therapeutically acceptable carrier. The single-chain variant antibody fragments are encoded by a nucleic acid sequence selected from the group consisting of SEQ ID NOs: 3, 4, 5 and 6.

The methods of the invention involve the treatment of an individual, preferably a patient, more preferably a mammalian patient and even more prefereably a human mammalian patient, having or suspected of having Huntington's disease by administering a therapeutically effective amount of an antibody, such as a single-chain variant fragment, or antibody composition comprising a single-chain variant fragment to the individual. The antibody compositions of the methods are preferably delivered intracranially, for example, by injection directly into brain tissue or by injection into the cerebrospinal fluid.

The methods of the invention may also involve the treatment of Huntington's disease by expressing anti-huntingtin antibodies, including single-chain variant fragments, in cells expressing mutant huntingtin protein. Nucleic acids encoding the subject antibodies and methods for their expression, including in therapeutic treatment protocols, are provided. Nucleic acids of the invention can be introduced into a host cell using various viral vectors and non-viral delivery techniques for expression of the nucleic acid encoding the antibody in brain tissue.

BRIEF DESCRIPTION OF THE DRAWINGS

FIG. 2 shows a diagram of the epitope mapping results from the peptide array analysis in FIG. 1. The results of the peptide array are displayed on a linear diagram of the normal human huntingtin amino acid sequence (SEQ ID NO: 1).

FIG. 5A shows the level of background immunostaining in the absence of primary antibody. FIG. 5B show immunostaining of MW1 and 1C2 antibodies in cortical neurons. FIGS. 5D and 5E shows immunostaining of MW1 and 1C2 antibodies in fresh frozen R6/1 cortex sections, respectively.

FIGS. 7E-7H show a confocal series of MW7 staining. MW6 shows punctate staining of the neuropil in WT (FIG. 7A) and R6/2 spinal cord while MW7 shows punctate staining of the perinuclear or nuclear membrane in WT (FIG. 7C) and R6/2 (FIG. 7D) brain. MW8 shows staining of neuronal inclusions in R6/2 (8-week old) fixed cortex sections (FIG. 7J).

FIG. 18B shows that the level of soluble Htt in the cleared lysates does not appear to be affected by expression of MW1, MW2 or MW7 scFv expression.

DETAILED DESCRIPTION OF THE PREFERRED EMBODIMENT

Figure 1:
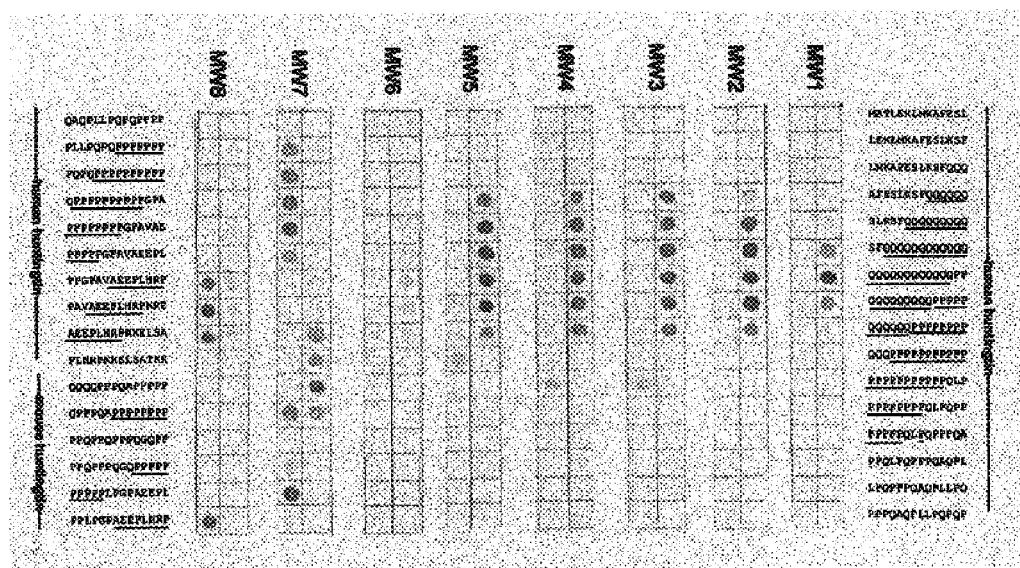
FIG. 1 shows epitope mapping of anti-huntingtin antibodies MW1-MW8 by peptide array which includes both human and mouse huntingtin peptides. Two rows of peptide dot blots are shown for each of the MW1-MW8 anti-huntingtin antibodies with the upper row corresponding to the peptides shown at the top of the figure, and the lower row corresponding to the peptides shown at the bottom of the figure. The three types of epitope of the huntingtin protein are underlined in the corresponding peptide sequences (__=polyQ; . . . =polyP; - - - =C terminus).

The huntingtin protein comprises a number of distinct regions that are believed to play a role in the toxicity of mutant Htt, as well as interaction of the Htt protein with other molecules. The present invention is based, in part, on the identification of antibodies directed to one or more distinct regions of the Htt protein that have desirable biological activities (Khoshnan et al. Proc. Natl. Acad. Sci. USA 99:1002-1007 (2002); Ko et al. Brain Res. Bull. 56:319-329 (2001), both of which are expressly incorporated herein by reference).

Antibodies, as well as other binding agents, including binding fragments and mimetics thereof (including intrabodies), that specifically bind to the Htt protein are provided. Preferred antibodies specifically bind to the polyglutamine ("polyQ") domain, polyproline ("polyP") domain or carboxy terminus of the huntingtin (Htt) protein.

Nucleic acid sequences encoding the subject antibodies, as well as methods for their expression, including in therapeutic treatment protocols, are also provided.

The preferred binding agents, e.g. antibodies, fragments and mimetics thereof, etc., bind to the huntingtin protein in a manner that differs in at least one aspect from the 1C2 antibody (Trottier et al., Nature, 10:104-110 (1995); Trottier et al., Nature, 378:403-406 (1995)). For example, and without limitation, the preferred antibodies may differ from the 1C2 antibody in terms of the epitope that they recognize or one or more of specificity, affinity and avidity.

Also provided are methods of screening compounds for the ability to modulate the activity of proteins comprising a polyglutamine repeat, particularly the huntingtin protein, as well as pharmaceutical compositions comprising such agents.

In addition, methods and devices are provided for screening samples for the presence of proteins comprising a polyglutamine repeat. In a particularly preferred embodiment, methods for identifying the presence of mutant huntingtin protein are provided. The methods may be used, for example, to diagnose a patient as someone who is, or is likely to suffer from Huntington's disease or a related disorder.

Definitions

Unless defined otherwise, technical and scientific terms used herein have the same meaning as commonly understood by one of ordinary skill in the art to which this invention belongs. See, e.g. Singleton et al., *Dictionary of Microbiology and Molecular Biology 2nd ed.*, J. Wiley & Sons (New York, N.Y. 1994); Sambrook et al., *Molecular Cloning, A Laboratory Manual*, Cold Springs Harbor Press (Cold Springs Harbor, N.Y. 1989). For purposes of the present invention, the following terms are defined below.

"Huntingtin" and "Htt" refer broadly to the huntingtin gene and the protein encoded by the huntingtin gene, including mutant and variant forms as well as native forms. "Variants" are biologically active polypeptides having an amino acid sequence which differs from the sequence of a native sequence polypeptide. Native sequence human huntingtin protein is described, for example, by The Huntington's Disease Collaborative Research Group in Cell 72:971-983 (1993) as well as in Li et al. Nature 378:398-402 (1995) and WO 02/29408. The number of polyglutamine repeats in native huntingtin protein is known to vary, from about 13 to about 36 glutamine residues in the polyQ region of native human protein. Native sequence murine Htt is described, for example, in Lin et al. Hum. Mol. Genet. 3 (1), 85-92 (1994) and typically comprises about 7 glutamine residues in the polyQ region. Particular variants of the huntingtin gene will comprise different numbers of CAG repeats, resulting in variation in the polyglutamine region of the huntingtin protein.

"Mutant huntingtin protein" refers to huntingtin protein which differs in some respect from the native sequence huntingtin protein. Typically, mutant huntingtin will comprise an expanded polyglutamine or polyproline region compared to the native form. A preferred mutant huntingtin protein has an expanded polyglutamine region of 40 or more glutamine residues.

As used herein, "nucleic acid" is defined as RNA or DNA that encodes a protein or peptide of the invention, particularly an antibody to the huntingtin protein, is complementary to a nucleic acid sequence encoding such peptides, hybridizes to such a nucleic acid and remains stably bound to it under appropriate stringency conditions, exhibits at least about 50%, 60%, 70%, 75%, 85%, 90% or 95% nucleotide sequence identity across the open reading frame, or encodes a polypeptide sharing at least about 50%, 60%, 70% or 75% sequence identity, preferably at least about 80%, and more preferably at least about 85%, and even more preferably at least about 90 or 95% or more identity with the peptide sequences. Specifically contemplated are genomic DNA, cDNA, mRNA and antisense molecules, as well as nucleic acids based on alternative backbones or including alternative bases whether derived from natural sources or synthesized.

As used herein, the terms nucleic acid, polynucleotide and nucleotide are interchangeable and refer to any nucleic acid, whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sultone linkages, and combinations of such linkages. The terms nucleic acid, polynucleotide and nucleotide also specifically include nucleic acids composed of bases other than the five biologically occurring bases (adenine, guanine, thymine, cytosine and uracil).

The terms "replicable expression vector" and "expression vector" refer to a piece of DNA, usually double-stranded, which may have inserted into it a piece of foreign DNA. Foreign DNA is defined as heterologous DNA, which is DNA not naturally found in the host cell. The vector is used to transport the foreign or heterologous DNA into a suitable host cell. Once in the host cell, the vector can replicate independently of the host chromosomal DNA, and several copies of the vector and its inserted (foreign) DNA may be generated. In addition, the vector contains the necessary elements that permit translating the foreign DNA into a polypeptide. Many molecules of the polypeptide encoded by the foreign DNA can thus be rapidly synthesized.

The term "control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancer.

Nucleic acid is "operably linked" when it is placed into a functional relationship with another nucleic acid sequence. For example, DNA for a presequence or a secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, then synthetic oligonucleotide adaptors or linkers are used in accord with conventional practice.

"Biological property" or "biological activity" is a biological function caused by an antibody or other compound of the invention. With regard to the anti-huntingtin protein antibodies, biological activity refers, in part, to the ability to specifically bind to the huntingtin protein. Other preferred biological activities include prevention of cell death or apoptosis, prevention of mutant huntingtin aggregation and the ability to regulate the toxic effects of mutant huntingtin protein that are associated with neurodegenerative disease.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules that lack antigen specificity.

Polypeptides of the latter kind are, for example, produced at low levels by the lymph system and at increased levels by myelomas.

"Antigen" when used herein refers to a substance, such as a particular peptide or protein, that can bind to a specific antibody. Preferred antigens include huntingtin protein, mutant huntingtin protein, and fragments thereof.

"Native antibodies" and "native immunoglobulins" are usually heterotetrameric glycoproteins, composed of two identical light (L) chains and two identical heavy (H) chains. Each light chain is linked to a heavy chain by one covalent disulfide bond. while The number of disulfide linkages varies among the heavy chains of different immunoglobulin isotypes. Each heavy and light chain also has regularly spaced intra-chain disulfide bridges. Each heavy chain has at one end a variable domain ($V_H$) followed by a number of constant domains. Each light chain has a variable domain at one end ($V_L$) and a constant domain at its other end. The constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The term "antibody" herein is used in the broadest sense and specifically covers human, non-human (e.g. murine) and humanized monoclonal antibodies, including full length monoclonal antibodies, polyclonal antibodies, multi-specific antibodies (e.g., bispecific antibodies), and antibody fragments, including intrabodies, so long as they exhibit the desired biological activity.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

"Antibody fragments" comprise a portion of a full-length antibody, generally the antigen binding or variable domain thereof. Examples of antibody fragments include Fab, Fab', F(ab')$_2$, and Fv fragments; diabodies; intrabodies; linear antibodies; single-chain antibody molecules; and multi-specific antibodies formed from antibody fragments.

The term "monoclonal antibody" as used herein refers to an antibody obtained from a population of antibodies wherein the individual antibodies comprising the population are identical except for possible naturally occurring mutations that may be present in minor amounts. Monoclonal antibodies are highly specific and are directed against a single antigenic site. In addition, monoclonal antibodies may be made by any method known in the art. For example, the monoclonal antibodies to be used in accordance with the present invention may be made by the hybridoma method first described by Kohler et al., Nature 256:495 (1975), or may be made by recombinant DNA methods (see, e.g., U.S. Pat. No. 4,816,567). The "monoclonal antibodies" may also be isolated from phage antibody libraries using the techniques described in Clackson et al., Nature 352:624-628 (1991) and Marks et al., J. Mol. Biol. 222:581-597 (1991), for example. The monoclonal antibodies herein specifically include antibody fragments, such as single-chain Fv or scFv antibody fragments.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass. Fragments of chimeric antibodies are also included provided they exhibit the desired biological activity (U.S. Pat. No. 4,816,567; and Morrison et al., Proc. Natl. Acad. Sci. USA 81:6851-6855 (1984)).

"Humanized" forms of non-human (e.g., murine) antibodies are antibodies that contain minimal sequence derived from non-human immunoglobulin. Humanized antibodies are generally human immunoglobulins in which hypervariable region residues are replaced by hypervariable region residues from a non-human species such as mouse, rat, rabbit or non-human primate having the desired specificity, affinity, and capacity. Framework region (FR) residues of the human immunoglobulin may be replaced by corresponding non-human residues. In addition, humanized antibodies may comprise residues that are not found in either the recipient antibody or in the donor antibody. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Reichmann et al., Nature 332:323-329 (1988); and Presta, Curr. Op. Struct. Biol. 2:593-596 (1992).

"Single-chain Fv" or "scFv" antibody fragments typically comprise the $V_H$ and $V_L$ domains of a monoclonal antibody, wherein these domains are present in a single polypeptide chain. Generally, the Fv polypeptide further comprises a polypeptide linker between the $V_H$ and $V_L$ domains which enables the scFv to form the desired structure for antigen binding. For a review of scFv see Pluckthun in The Pharmacology of Monoclonal Antibodies, vol. 113, Rosenburg and Moore eds. Springer-Verlag, New York, pp. 269-315 (1994).

The term "epitope" is used to refer to binding sites for (monoclonal or polyclonal) antibodies on protein antigens. There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. A competition ELISA assay is specifically described in Example 1. According to the gene fragment expression assays, the open reading frame encoding the protein is fragmented either randomly or by specific genetic constructions and the reactivity of the expressed fragments of the protein with the antibody to be tested is determined. The gene fragments may, for example, be produced by PCR and then transcribed and translated into protein in vitro, in the presence of radioactive amino acids. The binding of the antibody to the radioactively labeled protein fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. The latter approach is suitable to define linear epitopes of about 5 to 15 amino acids.

An antibody binds "essentially the same epitope" as a reference antibody, when the two antibodies recognize identical or sterically overlapping epitopes. The most widely used and rapid methods for determining whether two epitopes bind to identical or sterically overlapping epitopes are competition assays, which can be configured in all number of different formats, using either labeled antigen or labeled antibody. Usually, the antigen is immobilized on a 96-well plate, and the ability of unlabeled antibodies to block the binding of labeled antibodies is measured using radioactive or enzyme labels. A competition ELISA assay is disclosed in Example 1.

The term amino acid or amino acid residue, as used herein, refers to naturally occurring L amino acids or to D amino acids as described further below with respect to variants. The commonly used one- and three-letter abbreviations for amino acids are used herein (Bruce Alberts et al., Molecular Biology of the Cell, Garland Publishing, Inc., New York (3d ed. 1994)).

Hybridization is preferably performed under "stringent conditions" which means (1) employing low ionic strength and high temperature for washing, for example, 0.015 sodium chloride/0.0015 M sodium citrate/0.1% sodium dodecyl sulfate at 50° C., or (2) employing during hybridization a denaturing agent, such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C. Another example is use of 50% formamide, 5×SSC (0.75 M NaCl, 0.075 M sodium citrate), 50 mM sodium phosphate (pH 6/8), 0.1% sodium pyrophosphate, 5× Denhardt's solution, sonicated salmon sperm DNA (50 µg/ml), 0.1% SDS, and 10% dextran sulfate at 42° C., with washes at 42° C. in 0.2×SSC and 0.1% SDS.

As used herein, "treatment" is a clinical intervention made in response to a disease, disorder or physiological condition manifested by a patient, particularly Huntington's disease. The aim of treatment includes the alleviation or prevention of symptoms, slowing or stopping the progression or worsening of a disease, disorder, or condition and/or the remission of the disease, disorder or condition. "Treatment" refers to both therapeutic treatment and prophylactic or preventative measures. Those in need of treatment include those already affected by a disease or disorder or undesired physiological condition as well as those in which the disease or disorder or undesired physiological condition is to be prevented.

In the methods of the present invention, the term "control" and grammatical variants thereof, are used to refer to the prevention, partial or complete inhibition, reduction, delay or slowing down of an unwanted event, such as the presence or onset of Huntington's disease.

The term "effective amount" refers to an amount sufficient to effect beneficial or desirable clinical results.

The term "flag-tagged" when used herein refers to a chimeric polypeptide comprising a single-chain variable region fragment Ab (scFv) fused to a "flag epitope." The flag epitope has enough residues to provide an epitope against which an antibody may bind for detection purposes (Chiang et al., Pept. Res., 6:62-64 (1993)), but is also short enough such that it does not interfere with the activity of the scFv to which it is fused.

Antibodies to Huntingtin

Preferred antibodies are specific for particular epitopes on the huntingtin protein. The huntingtin protein comprises a polyglutamine-rich region close to the N-terminus of the protein, an adjacent polyproline-rich region and a carboxy-terminus region that is characterized by the sequence of SEQ ID NO: 2. DNA encoding the glutamine- and proline-rich regions of the human huntingtin protein are characterized by a polymorphic trinucleotide repeats. In particular, the polyglutamine region comprises a number of CAG repeats, encoding for glutamine residues. The CAG repeats are expanded on disease chromosomes. The adjacent polyproline region comprises polymorphic trinucleotide CCG repeats, encoding for prolines.

In the human huntingtin gene, the polymorphic CAG repeat region varies from 13 to 36 repeats and is encoded almost entirely by CAG. The mouse huntingtin gene encodes 7 consecutive glutamine residues in an imperfect repeat. In both species, the glutamine-rich region is followed by a segment with runs of prolines with interspersion of an occasional glutamine or other amino acid residue (Rubinsztein et al., Nat. Genet., 5(3):214-5 (1993), incorporated herein by reference). The polyproline regions of the huntingtin protein are well defined and found, for example, in SEQ ID NO: 5 in U.S. Pat. No. 5,693,757. These polyproline regions have sequences of at least 10 consecutive proline residues in the wild-type sequence.

More specifically, the preferred antibodies recognize an epitope within the polyglutamine-rich, polyproline-rich or carboxy-terminus domains of the huntingtin protein. By "recognize" it is meant that the antibodies bind to the huntingtin protein at the particular epitope. In many embodiments, the subject antibodies do not bind to any appreciable extent to proteins that do not share a significant degree of homology with the huntingtin protein.

The epitope specificity of the antibodies can be determined by epitope mapping as described, for example, in Ko et al., Brain Research Bulletin, 56:319-329 (2001) and in the Examples below.

Antibodies are preferably prepared by standard methods well-known in the art. The subject antibody compositions may be polyclonal, such that a heterogeneous population of antibodies differing by specificity is present, or monoclonal, in which a homogeneous population of identical antibodies that have the same specificity for the polyproline region of the huntingtin protein are present. As such, both monoclonal and polyclonal antibodies are provided by the subject invention. In many preferred embodiments, the subject antibodies are monoclonal antibodies. Specific monoclonal antibodies of interest include: MW1, MW2, MW7, MW8 and hMW9, where MW stands for "Milton Wexler," and are encoded by the nucleotide sequences of SEQ ID NO: 3, SEQ ID NO: 4, SEQ ID NO: 5 and SEQ ID NO: 6, respectively.

Generally, an antigen or immunogen that can elicit an immune response characterized by the presence of antibodies of the subject invention is employed. The immunogen preferably comprises at least includes a portion of a protein having a polyglutamine repeat region.

In one embodiment, the immunogen is at least a portion of a wild-type or mutant huntingtin protein, comprising a polyglutamine region having at least 19 glutamine repeats. The portion of the wild-type or mutant huntingtin protein may comprise exon 1 of the huntingtin protein, referred to herein as "HDx-1." A preferred HD-1x immunogen has the sequence of SEQ ID NO: 1, and comprises a polyglutamine region, a polyproline region and a carboxy-terminus region characterized by an eight amino acid stretch having the sequence AEEPLHRP (SEQ ID NO: 2).

In another embodiment, the immunogen is at least a portion of the wild-type or mutant dentatorubral palliodoluysian atrophy (DRPLA) protein (Onodera et al., FEBS Lett., 399:135-139 (1996)). The DRPLA protein preferably comprises a polyQ domain having from 19 to 35 glutamine repeats.

In the preferred embodiments, the immunogen is present in its aggregated state. In certain embodiments, other domains are also present in the immunogens. For example, a glutathione-S-transferase domain may be present in the immunogen (Onodera et al., FEBS Lett., 399:135-139 (1996); Harris, Methods Mol Biol, 88:87-99 (1998)). Other domains may be included. For example, domains may be included that serve to facilitate purification and identification of the antigen of interest. The immunogen is typically employed in the preparation of the subject antibodies as follows.

Although methods of making monoclonal and polyclonal antibodies are well known in the art, preferred methods are briefly described herein. Variations of the following methods will be apparent to one of skill in the art.

For preparation of polyclonal antibodies, the first step is immunization of the host animal with the immunogen. To increase the immune response of the host animal, the immunogen may be combined with an adjuvant. Suitable adjuvants include alum, dextran, sulfate, large polymeric anions, oil & water emulsions, e.g. Freund's adjuvant, Freund's complete adjuvant, and the like. The immunogen may also be conjugated to synthetic carrier proteins or synthetic antigens. A variety of hosts may be immunized to produce the polyclonal antibodies. Such hosts include without limitation, rabbits, guinea pigs, other rodents such as mice or rats, sheep, goats, primates and the like. The immunogen is administered to the host, usually intradermally, with an initial dosage followed by one or more, usually at least two, additional booster dosages. Following immunization, the blood from the host is collected, followed by separation of the serum from the blood cells. The Ig present in the resultant antiserum may be further fractionated using known methods, such as ammonium salt fractionation, DEAE chromatography, and the like.

As with the preparation of polyclonal antibodies, the first step in preparing monoclonal antibodies specific for an epitope within the huntingtin protein, is to immunize a suitable host. Suitable hosts include rats, hamsters, mice, monkeys and the like, and are preferably mice. Monoclonal antibodies may be generated using the hybridoma method described by Kohler et al., Nature, 256:495 (1975) or by recombinant DNA methods, such as those described in U.S. Pat. No. 4,816,567.

The immunogen is administered to the host in any convenient manner known in the art. For example, and without limitation, administration may be by subcutaneous injection with adjuvants, nitrocellulose implants comprising the immunogen or intrasplenic injections. Alternatively, lymphocytes may be immunized in vitro. The immunization protocol may be modulated to obtain a desired type of antibody, e.g. IgG or IgM, where such methods are known in the art (Kohler and Milstein, Nature, 256:495 (1975)). Booster immunizations may be made, for example one month after the initial immunization. Animals are bled and analyzed for antibody titer. Boosting may be continued until antibody production plateaus. Following immunization, plasma cells are harvested from the immunized host. Sources of plasma cells include the spleen and lymph nodes, with the spleen being preferred.

The plasma cells are then immortalized by fusion with myeloma cells to produce hybridoma cells. Fusion may be carried out by an electrocell fusion process or by using a suitable fusing agent, such as polyethylene glycol, to form a hybridoma cell (Goding, *Monoclonal Antibodies: Principles and Practice*, pp. 59-109, [Academic Press, 1996]). The plasma and myeloma cells are typically fused by combining the cells in a fusion medium usually in a ratio of about 10 plasma cells to 1 myeloma cell, where suitable fusion mediums include a fusion agent, e.g. PEG 1000, and the like. Following fusion, the fused cells will be selected, e.g. by growing on HAT medium.

A variety of myeloma cell lines are available. Preferably, the myeloma cell is HGPRT negative, incapable of producing or secreting its own antibodies, and growth stable. Preferred myeloma cells also fuse efficiently and support stable high-level production of antibody by the selected antibody-producing cells. Among these, preferred myeloma cell lines are murine myeloma lines, such as those derived from MOP-21 and MC.-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.* 133: 3001 (1984); Brodeur et al., *Monoclonal Antibody Production Techniques and Applications*, pp. 51-63, Marcel Dekker, Inc., New York, [1987]). Specific cell lines of interest include, for example, p3U1, SP 2/0 Ag14, P3.times.63Ag8.653 (Dr. Greenberg, V.A. Hospital).

Representative hybridomas according to the subject invention include those hybridomas that secrete one of the following monoclonal antibodies: MW1, MW2, MW7, MW8 and hMW9. Each of these antibodies is described in detail below.

Following hybridoma cell production, culture supernatant from individual hybridomas is screened for reactivity with huntingtin protein, particularly mutant huntingtin protein, using standard techniques. Such screening techniques are well known in the art and include radioimmunoassay (RIA), enzyme-linked immunosorent assay (ELISA), dot blot immunoassays, Western blots and the like. The binding affinity of the monoclonal antibody may, for example, be determined by the Scatchard analysis (Munson et al., Anal. Biochem., 107:220 (1980)).

After hybridoma cells secreting antibodies with the desired specificity, affinity and/or activity are selected, the cells may be subcloned by limiting dilution procedures and grown by standard methods (Goding, Monoclonal Antibodies: Principles and Practice, pp. 59-103, Academic Press, 1996). Culture media may be for example DMEM or RPMI-1640 medium. Alternatively, hybridomas may be grown in vitro as ascites tumors in an animal.

The desired antibody may be purified from the supernatants or ascites fluid by conventional techniques, e.g. affinity chromatography using mutant huntingtin protein bound to an insoluble support, protein A sepharose and the like.

DNA encoding the monoclonal antibody may be isolated and sequenced using conventional procedures, with the hybridoma cells serving as a source of the DNA. The isolated DNA may be introduced into host cells in culture to synthesize the monoclonal antibodies in the recombinant host cells. The DNA also may be modified, for example, by substituting the coding sequence for human heavy and light chain constant domains in place of the homologous murine sequences, Morrison, et al., *Proc. Nat. Acad. Sci.* 81, 6851 (1984), or by covalently joining to the immunoglobulin coding sequence all or part of the coding sequence for a non-immunoglobulin polypeptide. In that manner, "chimeric" or "hybrid" antibodies are prepared that have the binding specificity of an anti-Huntingtin protein described herein.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

Human monoclonal antibodies can be made by the hybridoma method. Human myeloma and mouse-human heteromyeloma cell lines for the production of human monoclonal antibodies have been described, for example, by Kozbor, *J. Immunol.* 133, 3001 (1984), and Brodeur, et al., *Monoclonal Antibody Production Techniques and Applications*, pp.51-63 (Marcel Dekker, Inc., New York, 1987).

It is now possible to produce transgenic animals (e.g. mice) that are capable, upon immunization, of producing a repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g. Jakobovits et al., *Proc. Natl. Acad. Sci. USA* 90, 2551-255 (1993); Jakobovits et al., *Nature* 362, 255-258 (1993).

Mendez et al. (*Nature Genetics* 15: 146-156 [1997]) have further improved the technology and have generated a line of transgenic mice designated as "Xenomouse II" that, when challenged with an antigen, generates high affinity fully human antibodies. This was achieved by germ-line integration of megabase human heavy chain and light chain loci into mice with deletion into endogenous $J_H$ segment as described above. The Xenomouse II harbors 1,020 kb of human heavy chain locus containing approximately 66 $V_H$ genes, complete $D_H$ and $J_H$ regions and three different constant regions (μ, δ and χ), and also harbors 800 kb of human κ locus containing 32 Vκ genes, Jκ segments and Cκ genes. The antibodies produced in these mice closely resemble that seen in humans in all respects, including gene rearrangement, assembly, and repertoire. The human antibodies are preferentially expressed over endogenous antibodies due to deletion in endogenous $J_H$ segment that prevents gene rearrangement in the murine locus.

Alternatively, phage display technology (McCafferty et al., *Nature* 348, 552-553 [1990]) can be used to produce human antibodies and antibody fragments in vitro, from immunoglobulin variable (V) domain gene repertoires from unimmunized donors.

Binding fragments or binding mimetics of the subject antibodies may also be prepared. These fragments and mimetics preferably share the binding characteristics of the subject antibodies. "Binding characteristics" when used herein include specificity, affinity, avidity, etc. for the huntingtin protein, particularly the polyglutamine, polyproline or c-terminal region of exon 1. The subject antibodies are modified to optimize their utility, for example for use in a particular immunoassay or their therapeutic use. In one embodiment antibody fragments, such as Fv and Fab may be prepared by cleavage of the intact protein, e.g. by protease or chemical cleavage. Nucleic acid encoding the antibody fragments or binding mimetics may be identified.

Antibody fragments, such as single chain antibodies or scFvs, may also be produced by recombinant DNA technology where such recombinant antibody fragments retain the binding characteristics of the above antibodies. "Antibody fragments" when used herein refer to a portion of an intact antibody, such as the antigen binding or variable region and may include single-chain antibodies, Fab, Fab', F(ab')2 and Fv fragments, diabodies, linear antibodies, and multispecific antibodies generated from portions of intact antibodies.

Recombinantly produced antibody fragments generally include at least the $V_H$ and $V_L$ domains of the subject antibodies, so as to retain the desired binding characteristics. These recombinantly produced antibody fragments or mimetics may be readily prepared from the antibodies of the present invention using any convenient methodology, such as the methodology disclosed in U.S. Pat. Nos. 5,851,829 and 5,965,371; the disclosures of which are herein incorporated by reference. The antibody fragments or mimetics may also be readily isolated from a human scFvs phage library (Pini et al., *Curr. Protein Pept. Sci.*, 1(2):155-69 (2000)) using huntingtin protein, particularly mutant huntingtin protein.

The invention also provides isolated nucleic acid encoding the anti-huntingtin antibodies, vectors and host cells comprising the nucleic acid, and recombinant techniques for the production of the antibodies.

For recombinant production of an antibody, the nucleic acid encoding it may be isolated and inserted into a replicable vector for further cloning and expression. DNA encoding the antibody is readily isolated and sequenced using conventional procedures. Many cloning and expression vectors are available and are well known in the art. The vector components generally include, but are not limited to, one or more of the following: a signal sequence, an origin of replication, one or more marker genes, an enhancer element, a promoter, and a transcription termination sequence, e.g., as described in U.S. Pat. No. 5,534,615.

Host cells, preferably eukaryotic cells such as CHO cell or COS cells, are transformed with the above-described expression or cloning vectors for anti-huntingtin antibody production and cultured according to well-established procedures.

Screening for Antibodies with Desired Properties

Once antibodies to the immunogen have been produced, they may be screened for desirable biological properties, such as high affinity binding to the desired antigen, specific binding to particular mutant forms of the huntingtin protein, the ability to prevent cell death or apoptosis associated with mutant huntingtin protein, and/or the ability to prevent aggregation of mutant huntingtin protein.

Prevention of Cell Death or Apoptosis

In a preferred embodiment, antibodies are identified that reduce the level of cell death associated with expression of mutant huntingtin protein. This activity may be observed in a model system for Huntington's disease, for example using terminal deoxynucleotidyltransferase-mediated dUTP nick end labeling (TUNEL) staining. Such an assay is described in Example 2, below and in Khoshnan et al., PNAS, 99:1002-1007 (2002), the entire contents of which are incorporated herein by reference in its entirety.

Specifically, extensive cellular DNA degradation is a characteristic event which often occurs in the early stages of apoptosis and is mediated by a Ca2+-dependent endonuclease. As cleavage of the DNA in apopototic cells results in double-stranded DNA fragments and single strand breaks, the degraded DNA may be detected by labeling methods. For example, enzymatic labeling of the free 3'-OH termini of the cellular DNA with modified nucleotides using exogenous enzymes, such as terminal deoxynucleotidyl transferase, is used to detect DNA strand breaks. The labeled DNA may be subsequently analyzed by immunocytochemistry (ICC), such as flow cytometry, fluorescence microscopy or light microscopy. Accordingly, preferred antibodies that reduce the level of apoptosis in a model system for Huntington's disease may be selected using the TUNEL staining.

Prevention of Mutant Huntingtin Aggregation

In a preferred embodiment of the invention, anti-huntingtin antibodies, particularly those that are directed to the polyproline region, are identified that have the ability to inhibit the aggregation of huntingtin in vivo. Aggregation of the huntingtin protein is associated with Huntington's disease and is present in affected neurons. Aggregation may be evaluated by examining the amount of huntingtin protein that is precipitated from cell lysates by centrifugation. The amount of aggregation is analyzed by subjecting the lysates that were subjected to centrifugation to SDS-PAGE. An exemplary assay is described in Example 2 and in Khoshnan et al., PNAS, 99:1002-1007 (2002).

Diagnostic Applications

The subject antibodies, binding fragments and mimetics thereof find use in immunoassays that are capable of providing for the detection of huntingtin or mutant huntingtin protein in a sample. In such assays, the sample suspected of comprising the huntingtin or mutant huntingtin protein of interest will typically be obtained from a subject, such as a human subject, suspected of suffering from the disease of interest or at risk for developing the disease of interest. The sample is generally a physiological sample from the patient such as blood or tissue. Depending on the nature of the sample, it may or may not be pretreated prior to assay, as will be apparent to one of skill in the art.

A number of different immunoassay formats are known in the art and may be employed in detecting the presence of protein of interest in a sample. Immunoassays of interest include Western blots on protein gels or protein spots on filters, where the antibody is labeled, as is known in the art. A variety of protein labeling schemes are known in the art and may be employed, the particular scheme and label chosen being the one most convenient for the intended use of the antibody, e.g. immunoassay. Examples of labels include labels that permit both the direct and indirect measurement of the presence of the antibody. Examples of labels that permit direct measurement of the antibody include radiolabels, such as $^3$H or $^{125}$I, fluorescent dyes, beads, chemilumninescers and colloidal particles. Examples of labels which permit indirect measurement of the presence of the antibody include enzymes where a substrate may provided for a colored or fluorescent product. For example, the antibodies may be labeled with a covalently bound enzyme capable of providing a detectable product signal after addition of suitable substrate. Instead of covalently binding the enzyme to the antibody, the antibody may be modified to comprise a first member of specific binding pair which specifically binds with a second member of the specific binding pair that in conjugated to the enzyme, e.g. the antibody may be covalently bound to biotin and the enzyme conjugate to streptavidin. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art.

Other immunoassays include those based on a competitive formats, as are known in the art. One such format would be where a solid support is coated with the polyproline region containing protein, including for example the mutant huntingtin protein. Labeled antibody is then combined with a sample suspected of comprising protein of interest to produce a reaction mixture which, following sufficient incubation time for binding complexes to form, is contacted with the solid phase bound protein. The amount of labeled antibody which binds to the solid phase will be proportional to the amount of protein in the sample, and the presence of protein may therefore be detected. Other competitive formats that may be employed include those where the sample suspected of comprising protein is combined with a known amount of labeled protein and then contacted with a solid support coated with antibody specific for the protein. Such assay formats are known in the art and further described in both Guide to Protein Purification, supra, and Antibodies, A Laboratory Manual (Cold Springs Harbor Press (Cold Springs Harbor, N.Y. 1989)).

In immunoassays involving solid supports, the solid support may be any compositions to which antibodies or fragments thereof can be bound, which is readily separated from soluble material, and which is otherwise compatible with the overall immunoassay method. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples.

Before adding patient samples or fractions thereof, the non-specific binding sites on the insoluble support i.e. those not occupied by the first antibody, are generally blocked. Preferred blocking agents include non-interfering proteins such as bovine serum albumin, casein, gelatin, and the like. Alternatively, detergents, such as Tween, NP40 or TX100 may be used at non-interfering concentrations.

It is particularly convenient in a clinical setting to perform the immunoassay in a self-contained apparatus, and such devices are provided by the subject invention. A number of such devices and methods for their use are known in the art. The apparatus will generally employ a continuous flow-path over a suitable filter or membrane, and will have at least three regions, a fluid transport region, a sample region, and a measuring region. The sample region is prevented from fluid transfer contact with the other portions of the flow path prior to receiving the sample. After the sample region receives the sample, it is brought into fluid transfer relationship with the other regions, and the fluid transfer region contacted with fluid to permit a reagent solution to pass through the sample region and into the measuring region. The measuring region may have bound to it a first antibody.

The second, labeled antibody combined with the assayed sample is introduced and the sandwich assay performed as above.

Screening to Identify Compounds with a Desired Biological Activity

The subject antibodies, binding fragments and mimetics thereof also find use in screening applications designed to identify agents or compounds that are capable of modulating, e.g. inhibiting, the binding interaction between the protein to which the antibody binds and a cellular target. For example, the subject antibodies find use in screening assays that identify compounds capable of modulating the interaction between mutant huntingtin protein and its cellular targets. In such assays, the subject antibody is contacted with mutant huntingtin protein in the presence of a candidate modulation agent and any resultant binding complexes between the antibody and the mutant huntingtin protein are detected. The results of the assay are then compared with a control. Those agents which change the amount of binding complexes that are produced upon contact are identified as agents that modulate the binding activity of mutant huntingtin protein and therefore are potential therapeutic agents. Of interest in many embodiments is the identification of agents that inhibit, at least to some extent, the binding of mutant huntingtin protein with its target. In many assays, at least one of the protein or antibody is attached to a solid support and at least one of these members is labeled, where supports and labels are described supra.

In other assays, the ability of a candidate compound to disrupt or enhance the biological activity of an anti-huntingtin antibody is measured. For example, the ability of a candidate compound to prevent or enhance the inhibition of cell death, apoptosis or aggregation normally produced by an anti-huntingtin antibody may be measured.

A variety of different candidate agents may be screened by the above screening methods. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Methods of Treatment

An individual suffering from Huntington's disease may be treated using antibodies of the present invention or compounds identified in screens using the antibodies. By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as neuronal cell death. As such, treatment includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of individuals are treatable according to the subject methods. Generally such individuals are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the individuals will be humans.

In certain embodiments, the methods of treatment involve administration of an effective amount of a compound that modulates, e.g. inhibits, the interaction of a mutant huntingtin protein, with its cellular targets. The compound is preferably an antibody of the invention that targets the polyproline region of the huntingtin protein, the polyglutamine region of the huntingtin protein or an epitope within the c-terminal sequence of exon 1 of the huntingtin protein. In a preferred embodiment the antibodies are human or humanized, such that any undesirable immune response in the patient is minimized.

The anti-huntingtin antibodies may be administered using any convenient protocol capable of resulting in the desired therapeutic activity. Thus, the agent can be incorporated into a variety of formulations for therapeutic administration. More particularly, the agents of the present invention can be formulated into pharmaceutical compositions by combination with appropriate, pharmaceutically acceptable carriers or diluents (Remington: The Science and Practice of Pharmacy, 19$^{th}$ Edition, Alfonso, R., ed., Mack Publishing Co. (Easton, Pa.: 1995)), and may be formulated into preparations in solid, semi-solid, liquid or gaseous forms, such as tablets, capsules, powders, granules, ointments, solutions, suppositories, injections, inhalants and aerosols.

Anti-huntingtin protein antibodies can also be administered by inhalation. Commercially available nebulizers for liquid formulations, including jet nebulizers and ultrasonic nebulizers are useful for such administration. Anti-huntingtin protein antibodies can also be aerosolized using a fluorcarbon formulation and a metered dose inhaler, or inhaled as a lyophilized and milled powder.

The anti-huntingtin antibodies to be used for in vivo administration must be sterile. The sterility may be accomplished by filtration using sterile filtration membranes, prior to or following lyophilization and reconstitution. The anti-huntingtin antibodies may be stored in lyophilized form or in solution.

The anti-huntingtin antibody compositions may be placed into a container with a sterile access port, for example, an intravenous solution bag or vial having a stopper pierceable by a hypodermic injection needle.

In pharmaceutical dosage forms, the antibodies or other compounds may be used alone or in appropriate association, as well as in combination with other pharmaceutically active or inactive compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Each dosage for human and animal subjects will preferably contain a predetermined quantity of compounds of the present invention calculated in an amount sufficient to produce the desired effect, in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, antioxidants, low molecular weight (less than about 10 residues) polypeptides, tonicity adjusting agents, stabilizers, wetting agents and the like, are readily available to the public. "Carriers" when used herein refers to pharmaceutically acceptable carriers, excipients or stabilizers which are nontoxic to the cell or mammal being exposed to the carrier at the dosages and concentrations used.

Administration of the agents can be achieved in various ways, including intracranial, either injected directly into the brain tissue or injected into the cerebrospinal fluid, oral, buccal, rectal, parenteral, intraperitoneal, intradermal, transdermal, intracheal, intracerebral, etc., administration. The antibodies may be administered in combination with one or more additional therapeutic agents. Administration may be chronic or intermittent, as deemed appropriate by the supervising practitioner, particularly in view of any change in the disease state or any undesirable side effects. Administration "in combination with" one or more further therapeutic agents includes both simultaneous (at the same time) and consecutive administration in any order. "Chronic" administration refers to administration of the agent in a continuous manner while "intermittent" administration refers to treatment that is not done without interruption.

In a particular embodiment, antibodies of the invention are administered by intracranial injection. The injection will typically be directly into affected brain regions or into the cerebrospinal fluid.

An effective amount of an antibody or compound of the present invention to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1 µg/kg to up to 100 mg/kg or more, depending on the factors mentioned above. Typically, the clinician will administer a molecule of the present invention until a dosage is reached that provides the required biological effect. The progress of this therapy is easily monitored by conventional assays.

Also provided by the subject invention are methods of treating Huntington's disease conditions by expressing antibodies, particularly intrabodies, i.e. non-secreted forms of the subject antibodies, e.g. scFv analogs of the subject antibodies, as described supra, in cells expressing mutant huntingtin protein. Intrabodies and methods for their use in the treatment of disease conditions are described in U.S. Pat. Nos. 5,851,829 and 5,965,371, the disclosures of which are herein incorporated by reference. In such methods, a nucleic acid encoding the antibody or intrabody, generally in the form of an expression cassette that includes a sequence encoding the antibody domains of interest, such as the $V_H$ and $V_L$ domains, as well as other components, e.g. promoters, linkers, intracellular localization domains or sequences, etc., is introduced into the target cells in which antibody or intrabody production is desired. The nucleic acid is introduced into the target cells using any convenient methodology, e.g. through use of a vector, such as a viral vector, liposome vector, by biolistic transfection and the like, where suitable vectors are well known in the art. Viral and/or non-viral methods of delivering the nucleic acid encoding the intrabody to the cell may be used.

A wide variety of non-viral vehicles for delivery of a polynucleotide encoding an antibody of the present invention are known in the art and are encompassed in the present invention. A nucleic acid encoding an anti-huntingtin antibody or intrabody can be delivered to a cell as naked DNA (U.S. Pat. No. 5,692,622; WO 97/40163). Alternatively, a the nucleic acid can be delivered to a cell by association with one or more of a variety of substances including, but not limited to cationic lipids; biocompatible polymers, including natural polymers and synthetic polymers; lipoproteins; polypeptides; polysaccharides; lipopolysaccharides; artificial viral envelopes; metal particles; and bacteria. The nucleic acid could also be delivered as a microparticle. Mixtures or conjugates of these various substances can also be used as delivery vehicles. The nucleic acid can be associated non-covalently or covalently with these delivery agents. It is possible to target liposomes to a particular cell type.

Viral vectors include, but are not limited to, DNA viral vectors such as those based on adenoviruses, herpes simplex virus, poxviruses such as vaccinia virus, and parvoviruses, including adeno-associated virus; and RNA viral vectors, including, but not limited to, retroviral vectors. Retroviral vectors include, for example, murine leukemia virus, and lentiviruses such as human immunodeficiency virus. Naldini et al., *Science* 272:263-267 (1996).

In a particular embodiment, the nucleic acid encoding the intrabody that is to be expressed is inserted into a viral vector. Preferred viral constructs are based on a retroviral genome, more preferably a lentiviral genome as these viruses are able to infect both dividing and non-dividing cells. The vector is transfected into packaging cells and recombinant retrovirus is collected. The recombinant retrovirus is then contacted with the cells in which expression of the intrabody is desired. For example, the virus may be injected intracranially or into the cerebrospinal fluid. In a particular embodiment, the virus is injected directly into brain regions that are known to be affected by Huntington's disease.

Following introduction of the nucleic acid into the target cells, the nucleic acid is allowed to be expressed in the target cell, whereby intrabodies that specifically bind to the protein of interest, e.g. mutant huntingtin protein, are produced in the cell. Production of the intrabodies interferes with the activity of the protein, e.g. mutant huntingtin protein, and thereby treats the host suffering from the disease condition.

EXAMPLES

Further details of the invention can be found in the following example, which further defines the scope of the invention. The following examples, including the experiments conducted and achieved are provided for illustrative purposes only and are not to be construed as limiting upon the present invention. All references cited throughout the specification, are hereby expressly incorporated by reference in their entirety.

Example 1

Anti-Huntingtin Antibodies

A. Production of Anti-Huntingtin Antibodies

The antigens used and the isotypes of the MW monoclonal anti-huntingtin antibodies are summarized in Table 1.

1. Immunization

For generation of anti-huntingtin antibodies, six-week-old Balb/c female mice were primed and boosted at 2 week intervals by intraperitoneal injection of antigen emulsified in adjuvant (RIBI Immunochem, Hamilton, Mont., USA). Three different methods were used for the generation of the anti-huntingtin antibodies.

a. DRPLA-19Q or DRPLA-35Q

For generation of mAbs, herein referred to as MW (for Milton Wexler) mAbs, MW1, MW2 and MW5, mice were injected with antigen proteins that were expressed from two constructs comprising the polyQ domain (19 or 35 repeats) of huntingtin and 34 amino acids of the dentatorubralpalliodoluysian atrophy (DRPLA) gene fused to glutathione-S-transferase (GST) (Onodera et al., FEBS Lett, 399:135-139 (1996)). Test bleeds were obtained 7 days after very other injection. A final series of boosts were performed without adjuvant. Spleen cells were isolated from the mouse 3 days after the final boost and fused with HL-1 murine myeloma cells (Ventrex, Portland, Me. USA) using polyethylene glycol (PEG 1500, Boehringer-Mannheim, Mannheim, Germany) (Lebron et al., J. Immunol., 222:59-63 (1999)). Using enzyme linked substrate assay (ELISA) to screen against these antigens versus GST alone, three hybridomas were selected for cloning.

b. Expanded PolyQ Domain of Exon 1 of Huntingtin Protein in Soluble Form

For generation of mAbs, MW3, MW4 and MW6, mice were immunized as described above with protein that was soluble in aqueous solution and was expressed from a construct comprising the expanded polyQ domain (67 glutamine repeats) of Htt exon 1 (67Q) fused to GST (GST-HDx67Q). Spleen cells were isolated from the mice 3 days after the final boost and fused with HL-1 murine myeloma cells.

c. Expanded PolyQ Domain of Exon 1 of Huntingtin Protein in Soluble and Aggregated Form For generation of mAbs, MW7 and MW8, mice were immunized with the same Htt exon 1 (67Q) protein fused to GST (GST-HDx67Q). However, boosting of the mice was performed with an aggregated form of exon 1 having 67 Q repeats of the huntingtin protein (67Q), prepared by removing the GST. Spleen cells were isolated from the mice 3 days after the final boost and fused with HL-1 murine myeloma cells.

2. Selection of Hybridomas

Three hybridomas generated from mice immunized with proteins expressed from the two constructs containing the polyQ domain (19 or 35 repeats) and 34 amino acids of the dentatorubralpalliodoluysian atrophy (DRPLA) gene fused to glutathione-S-transferase (GST) were selected for cloning. mAbs from these hybridomas were termed MW1, MW2, and MW5.

The hybridomas generated from mice immunized with GST-HDx67Q, and from mice immunized with the same GST-HDx67Q antigen and boosted with an aggregated form that lacked the GST were both screened by ELISA using the antigen, GST-HDx67Q and GST alone, and by Western blotting of extracts from the Huntington's disease (HD) lymphoblastoma cell line HD2. mAbs, MW3, MW4 and MW6 were generated from hybridomas generated from mice immunized with GST-HDx67Q while mAbs, MW7 and MW8 were generated from hybridomas generated from mice immunized with GST-HDx67Q and boosted with an aggregated form of GST-HDx67Q that lacked GST.

a. ELISA

The hybridomas were analyzed by ELISA using the antigen, GST-HDx67Q and GST alone. MW3, MW4 and MW6 bound the injected protein, GST-HDx67Q, but did not bind to GST alone. MW7 and MW 8 were selected for having a positive ELISA signal with GST-HDx67Q.

b. Western Blots

Figure 3:
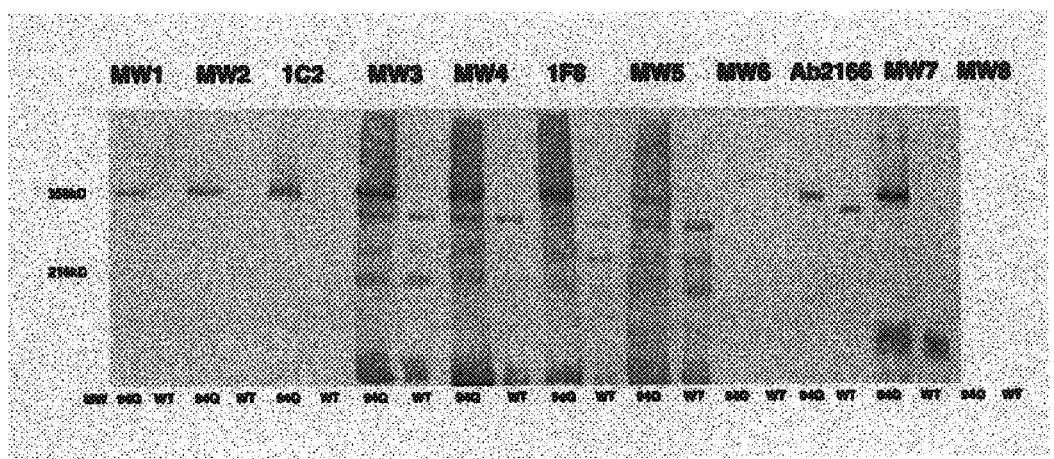
FIG. 3 shows a Western blot of normal (WT) and transgenic 94Q knock-in (94Q) mouse cerebellum extracts using anti-huntingtin antibodies MW1-MW8. Control antibodies 1C2 and 1F8 were used to identify mutant huntingtin protein, and 2166 antibody was used to identify both mutant and normal huntingtin protein.
Figure 4:
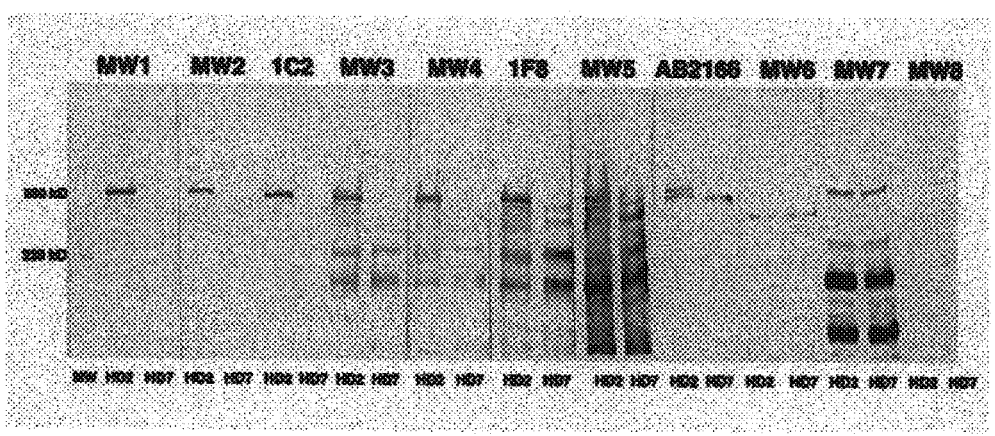
FIG. 4 shows a Western blot of normal (HD7) and Huntington's disease (HD2) human lymphoblastoma cell extracts using anti-huntingtin antibodies MW1-MW8. Control antibodies 1C2 and 1F8 were used to identify mutant huntingtin protein, and 2166 antibody was used to identify both mutant and normal huntingtin protein.

For the Western blots, lymphoblasts from control (HD7) and HD patients (HD2) were cultured in Isscove's modified Dulbecco's medium (Irvine Scientific, Irvine, Calif. USA) supplemented with 15% fetal calf serum and 2 mM glutamine. Lymphoblasts or cerebella from mice were homogenized in 300 mM NaCl, 1 mM EDTA, 0.5% Triton X-100, 50 mM Tris, pH 7.0, with complete protease inhibitor cocktail (Boehringer Mannheim). The homogenates were centrifuged (14,300 rpm for 10 min). The protein concentrations of the supernatants were determined BCA assay (Pierce, Rockford, Ill., USA). The protein in the supernatants were concentrated by precipitation at 70° C. for 3 min. The precipitates were resuspended in 6 M urea at one half of the original supernatant volume and concentrated sodium dodecyl sulfate (SDS) dissociation buffer added to achieve a final concentration of 5% 2-mercaptoethanol, 1.5% SDS, and 5% glycerol. Samples were heated at 95° C. for 10 minutes and subjected to SDS polyacrylamide gel electrophoresis (PAGE) on 5% gels (Laemmlie, E. K., Nature, 227:105-132 (1970)). Gels were electrotransferred to nitrocellulose membrane (Schleicher & Schuell, Keene, N.H., USA) overnight with cooling. These membranes were then preblocked with 1% blocking reagent (Boehringer Mannheim) and incubated with the MW mAbs (undiluted hybridoma supernatants), MAB2166 (Chemicon, Temecula, Calif., USA; 1/1000 dilution), 1F8 ascites fluid (M. MacDonald; 1/1000 dilution), overnight at room temperature. Blots were washed with 0.5% Tween-20 in phosphate-buffered saline (PBS) for 10 minutes 3 times before incubation with biotinylated goat anti-mouse immunoglobulin (Ig) G+IgM (Chemicon), diluted 1/1000 in blocking buffer, for 1 hour at room temperature. After washing, the blots were incubated with horseradish peroxidase-strepavidin (Chemicon) in blocking buffer for 1 hour at room temperature. Blots were developed using 4-chloro-1-naphthol.

expanded polyQ, the MW1-MW8 mAbs were tested in parallel for binding, as analyzed by immunoblotting, to brain extracts of a wild-type mouse and a knock-in transgenic mouse that expresses a mouse human chimeric Htt exon 1 construct that contains 94Q repeats (94Q knock-in mouse) (Menalled et al., Exp. Neurol., 162:328-342 (2000)) (FIG. 3) and extracts of a lymphoblastoma cell line from a human HD patient (HD2) that expressed both normal and mutant Htt and a lymphblastoma cell line from human non-HD patient (HD7) that expressed only normal Htt (FIG. 4). Control antibodies, 1C2 (Chemicon MAb1574; Trottier et al., Nat. Genet., 10:1040110 (1995)) and 1F8 (Wheeler et al., Hum. Mol. Genet., 9:503-513 (2000)) were used to identify mutant Htt, and Ab2166 (Chemicon) were used to identify both mutant and normal Htt.

TABLE 1

GENERATION AND CHARACTERIZATION OF ANTI-HUNTINGTIN (Htt) MONOCLONAL ANTIBODIES (mAbs)

| Antigen | MAb | Isotype | Epitope | Immunoblot | ICC |
|---|---|---|---|---|---|
| DRPLA-19Q | MW1 | IgG2b | polyQ | Mutant Htt | Cytoplasm |
| DRPLA-35Q and | MW2 | IgM | polyQ | Mutant Htt | Golgi |
| TRX-35Q | MW5 | IgM | polyQ | Mutant Htt + other bands | Golgi |
| HDx-67Q (soluble) | MW3 | IgM | polyQ | Mutant Htt + other bands | Golgi |
|  | MW4 | IgM | polyQ | Mutant Htt + other bands | Golgi |
|  | MW6 | IgM | polyQ | Band below 350 kD + variable size band | Cytoplasm |
| HDx-67Q (soluble 1st and boost with aggregate) | MW7 | IgM | polyP | 350 kD + 130 kD and lower | Perinuclear in wild-type mouse brain; inclusions in R6/2 brain |
|  | MW8 | IgG2a | AEEPLHRPK | ? | No staining in wild-type mouse brain; inclusions in R6/2 brain |

B. Characterization of Anti-Htt Antibodies

1. Epitope Mapping

To determine the epitopes recognized by these mAbs, we utilized arrays of dot blots that contain overlapping 14mer peptides synthesized from the first 91 amino acids of normal human Htt (containing a 23 polyQ domain). The first dot contained the peptide corresponding to amino acids 1-14, the second dot contained the peptide corresponding to 4-17, the third dot contained the peptide corresponding to 7-20, etc.

Each of the MW1-MW6 mAbs specifically bound one of three single, contiguous epitopes in the Htt sequence (FIG. 1). MW1-MW6 bound peptides that contain >6 glutamines and were specific for the polyQ region. As the antigens used to generate the MW1-MW6 mAbs contained other amino acids in numbers equal or greater than the polyQ domain, the polyQ domain may be highly antigenic or may be prominently displayed in soluble protein fragments.

As summarized in FIG. 2, MW7 specifically binds peptides that contain the polyP domain in Htt. There are two of these domains in exon 1, and MW7 binds all peptides with >5 consecutive prolines. MW8, in contrast, binds specifically to an eight amino acid stretch, AEEPLHRP (SEQ ID NO: 2), near the Cterminus of exon 1. MW7 and MW8 mAbs did not bind the polyQ domain in Htt.

2. Western Blots

To determine if MW1-MW8 mAbs were able to distinguish between normal and mutant Htt containing the expanded polyQ, the MW1-MW8 mAbs were tested in The extracts used and the procedure for immunoblotting was performed as described above.

MW1-MW6 specifically bound the polyQ epitope in Htt with MW1-MW5 preferentially binding to the expanded repeat mutant form of Htt rather than normal Htt on Western blots. More specifically, the mAbs MW1 and MW2 displayed a very specific binding pattern similar to the pattern for 1C2, strongly staining the expanded mutant polyQ form of Htt that is approximately 350 kD in size in mouse brain extracts from the 94Q mice and did not bind the normal polyQ form in mouse brain extracts from WT mice (FIG. 3). MW1 and MW2 mAbs also specifically bound the 350 kDa form of mutant Htt in extracts from HD2 cells (FIG. 4).

MW3-MW5 displayed a very specific binding pattern similar to the pattern for 1F8 in mouse brain extracts. MW3-MW5 specifically bound the expanded mutant repeat form of Htt rather than normal Htt as well as other bands of lower molecular weights which may be breakdown products of Htt with different conformations (FIG. 3). MW3-MW5 mAbs also specifically bound the 350 kDa form of mutant Htt in extracts from HD2 cells (FIG. 4).

MW6 specifically bound in normal and HD human lymphoblastoma cell extracts an antigen that has a size varying from about 250-300 kDa which may be a breakdown product of Htt.

MW7 bound the expanded repeat mutant form of Htt in mouse brain extracts (FIG. 3). In human lymphoblastoma cell extracts, MW7 bound the high molecular weight Htt very weakly, but binds strongly one or two smaller molecular weight proteins which are present in normal (HD7) and Huntington's disease (HD2) human lymphoblastoma cell extracts (FIG. 4) at roughly equivalent levels.

MW8 did not detectably bind any proteins in mouse brain extracts nor in human lymphoblastoma cell extracts examined by immunoblotting.

3. Immunostaining

Light microscopic immunohistochemistry was done with 10-μm sections of 4% paraformaldehyde fixed R6/2 tissue or fresh frozen R6/1 tissue. Briefly, 8-10-week-old R6/1, R6/2 or control littermates (Jackson Laboratory; Mangiarini et al., Cell, 87:493-506 (1996)) were anesthetized with Phenobarbital, perfused with PBS followed by 4% paraformaldehyde or PBS only. Brains were removed and frozen on dry ice with O.C.T. compound (Sakura Finetek, Torrance, Calif., USA). R6/2 contains human Htt exon 1 with 144 polyQ repeats while R6/1 contains 116 repeats and displays symptoms at a later age than R6/2. Fixed sections were incubated with mAbs MW3-8 or 1F8(1/1000). PBS washed sections were incubated with Hi-Fluorescence goat anti-mouse IgG (Antibodies, Inc., Davis, Calif., USA) and DTAF goat anti mouse IgG+IgM (Chemicon) in blocking buffer (2% bovine serum albumin, 5% normal goat serum). Fresh frozen sections were incubated with ascites of MW1 or MW2 at 1/1000, or 1C2 (Chemicon MAB1574) at 1/1000, in blocking buffer. Biotinylated goat anti-mouse IgG+IgM and fluorescein isothiocyanatestreptavidin were used. Light microscopic images were captured using a digital camera (SPOT, Diagnostic Instruments, Sterling Heights, Mich., USA) attached to an epi-fluorescent microscope (Leica DMLB, Deerfield, Ill., USA). Thirty-five micrometer 4% paraformaldehyde fixed floating sections were processed using the same secondary Abs as above and subjected to confocal microscopy (Leica DM IRB/E, Leica confocal software).

Figure 5:
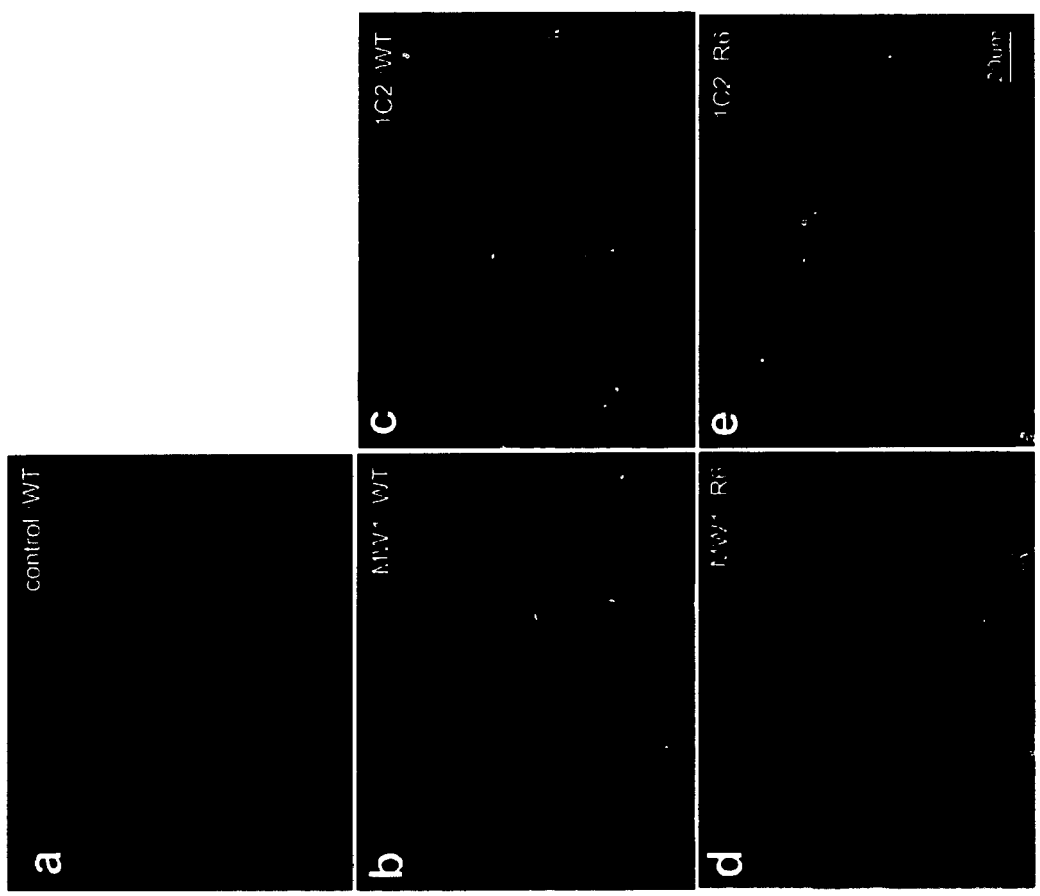
FIGS. 5A-5E show immunofluorescence staining patterns of MW1 anti-huntingtin and control 1C2 antibodies in wild-type (WT) and R6/2 transgenic cortex (R6), having mutant spinal cord neurons.

MW1 and control 1C2 antibodies displayed primarily punctate cytoplasmic staining of neurons (FIGS. 5B and 5D) in wild-type and R6/2 transgenic brain sections. Neuropil staining with MW1 which was also apparent was specific because controls omitting the primary antibody were largely negative under the same staining and photographic conditions (FIG. 5a).

Figure 6:
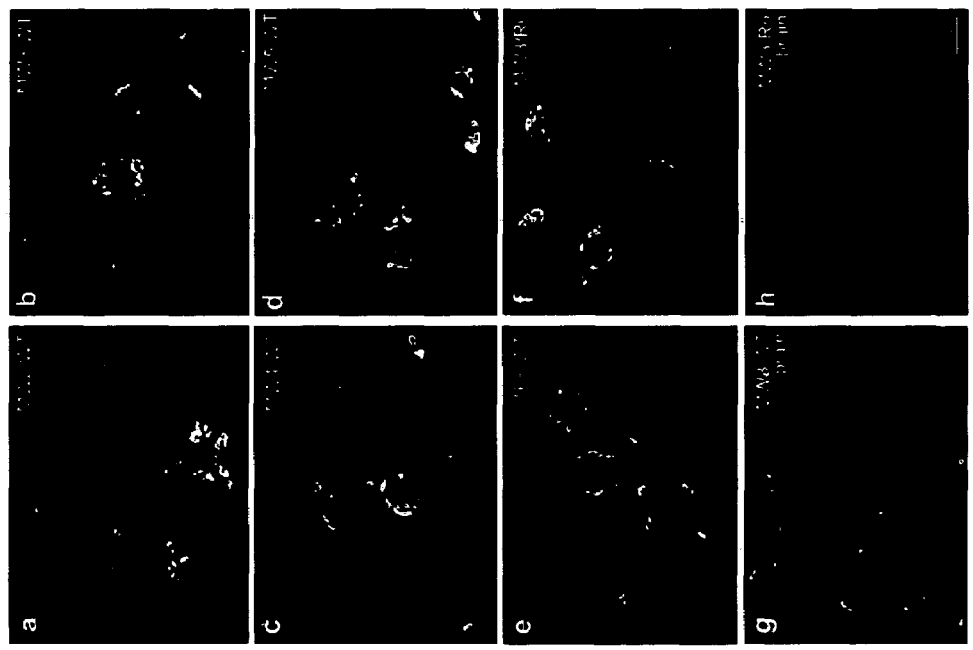
FIGS. 6A-6H show immunofluorescence staining patterns of MW2-MW5 anti-huntingtin and control 1F8 antibodies in wild-type (WT) and R6/2 transgenic cortex (R6), having mutant spinal cord neurons. MW2 (FIG. 6A), MW3 (FIG. 6B), MW4 (FIG. 6C), MW5 (FIG. 6D) and control 1F8 (FIG. 6E) antibodies exhibit similar patterns, neuronal Golgi complex staining, when used to stain spinal cord sections. MW3 staining of paraformaldehyde fixed spinal cord sections from R6/2 mice is shown in FIG. 6F. MW3 staining of wild-type and R6/2 mutant brain sections are shown in FIGS. 6G and 6H, respectively.

MW2-MW5 and control 1F8 antibodies displayed little or no staining of the neuropil, but stained neuronal Golgi complex in wild-type spinal cord section as shown in FIGS. 6A-6E and in R6/2 transgenic spinal cord sections (MW3 staining is shown in FIG. 6F) with no difference in staining between wild-type and mutant transgenic spinal cord with MW3-MW5 antibodies. However, MW3, MW4 and MW5 staining in R6/2 brain sections (MW3 staining is shown in FIG. 6H) was less than staining in wild-type brain sections (MW3 staining is shown in FIG. 6G).

MW6 displayed very strong punctate staining of neuropil and strong homogeneous staining of neuronal cytoplasm in wild-type (FIG. 7A) and mutant spinal cord (FIG. 7B), with no obvious difference in staining between wild-type and mutant spinal cord. MW6 antibodies did not strongly stain neuronal nucleus.

MW7 displayed punctate perinuclear or nuclear membrane staining in wild-type (FIG. 7C) and mutant brain sections (FIG. 7D) with weaker punctate perinuclear or nuclear membrane staining, but more prominent nuclear inclusion staining in mutant R6/2 brain sections. The perinuclear staining is shown in a confocal microscope series (FIGS. 7E-7H).

Figure 7:
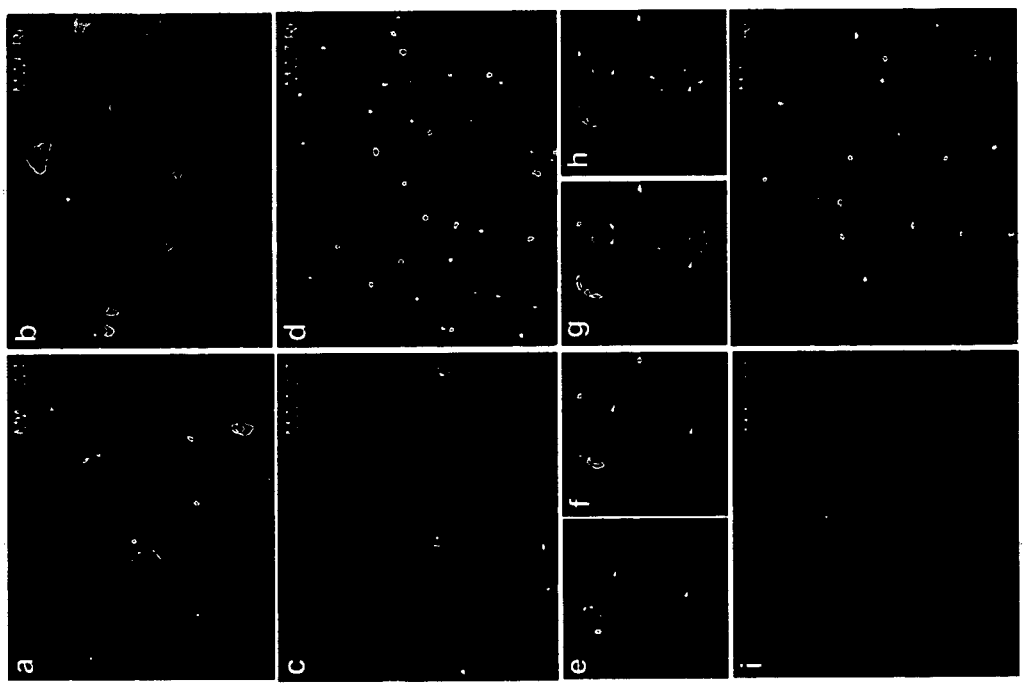
FIGS. 7A-7I show immunofluorescence staining patterns of MW6-MW8 anti-huntingtin antibodies in wild-type (WT) and mutant transgenic R6/2 (R6) spinal cord and brain.

MW8 mAbs displayed nuclear inclusion staining in R6/2 brain sections (FIG. 7J), but did not stain nuclear inclusions in wild-type brain sections (FIG. 7I). MW8 mAbs also stained small inclusions in the neuropil.

In summary, MW1-MW6 mAbs did not stain nuclear inclusions well in brain sections while MW7 and MW8 mAbs stained nuclear inclusions in brain sections of mice expressing a human chimeric Htt exon1 construct with 94Q repeats.

4. Summary

Figure 8:
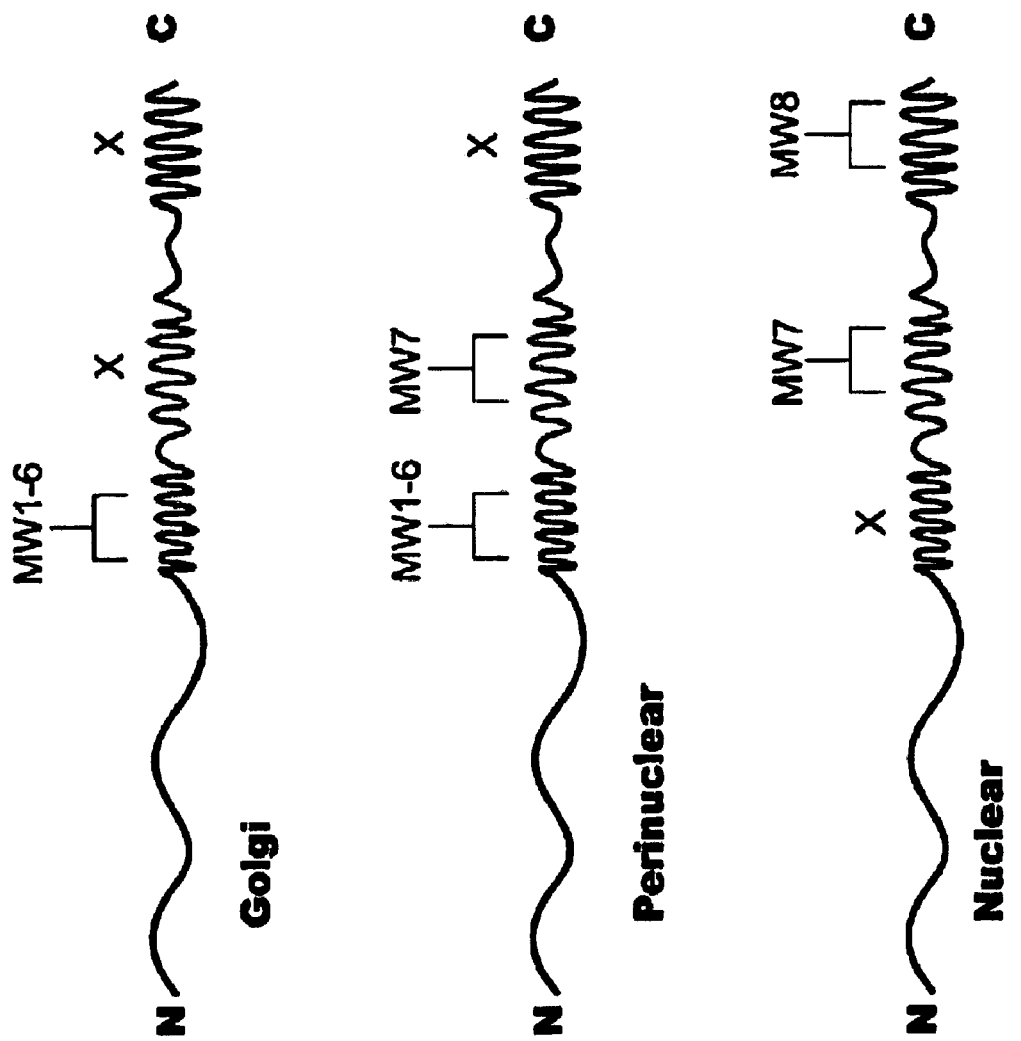
FIG. 8 shows a diagram illustrating the binding patterns of the MW1-MW8 anti-huntingtin antibodies to the huntingtin protein as analyzed by peptide array and immunohistochemical staining in vivo. The domain structure of the diagram of the huntingtin protein is from left to right as follows: the N-terminus, the polyQ domain, the polyP domain and the C-terminus.

Both the epitope mapping and histochemical results are summarized in FIG. 8. The availability of four regions of exon 1 of Htt, the N-terminal 17 amino acids, the polyQ domain, the polyP domain and the C-terminal domain, for Ab binding was different in the Golgi, perinuculear and nuclear subcellular compartments. The N-terminal 17 amino acids of exon 1 of Htt was available for Ab binding in the Golgi, perinuclear and nuclear subcompartments. In the spinal cord neuronal Golgi complex of both WT and R6/2 mice, the polyQ domain was available, but the adjacent polyP and C-terminal domains were occluded. In the perinuclear region of neurons of R6/2 mice, the polyP domain was available for Ab binding, but the C-terminus was occluded. Within the nucleus of neurons in the R6/2 (but not wild-type) mice, the polyQ domain was occluded, but the adjacent N-terminal, C-terminal and polyP domains were open for Ab binding.

Example 2

Anti-Htt Antibody Fragments

To examine the effects of the anti-huntingtin (Htt) antibodies on the biological activities of Htt exon 1, we generated single-chain variable region fragment Abs (scFvs) for MW1 and MW2 anti-Htt antibodies, which recognizes the polyQ Http epitope, MW7 anti-Htt antibody, which recognizes the polyP domains of Htt exon 1 and MW8 anti-Htt antibody, which recognizes an 8 amino acid epitope near the C-terminus of the huntingtin protein. Human anti-huntingtin hMW9 antibody was isolated from a human scFvs phage library using recombinant mutant huntingtin protein. The scFvs for MW1, MW2, MW7 and MW8, expressed in *E. coli* were tested for binding to Htt on immunoblots, and the scFv for hMW9 were tested for binding to His-HDx in vitro. Positive clones were selected for further characterization in mammalian cells.

A. Generation of scFvs

1. MW1, MW2, MW7 and MW8 scFvs

For generation of MW1, MW2, MW7 and MW8 scFvs, total RNA was extracted from hybridoma cell lines secreting each of the anti-Htt MW mAbs, and mRNA was purified by using oligo-dT columns (Qiagen, Valencia, Calif.). Complementary cDNA was produced for each mRNA pool by using random hexanucleotide primers. The cDNAs served as sources of DNA to amplify both variable region heavy (VH) and variable region light (VL) chains for each mAb by using primers complementary to the consensus sequences flanking each domain (Amersham Pharmacia) and PCR technology. To generate recombinant single-chain fragment Abs, the amplified VH and VL of each mAb were linked by a 45-mer nucleotide encoding Gly-Ser. These scFv genes were cloned into the M13 phagemid, pCANTBE5 (Amersham Pharmacia), and used to transform *Escherichia coli*, strain TG15, which supports production of recombinant phage. The amplified recombinant phage population was selected for binding on immunoblots to Htt exon-1-glutathione S-transferase (GST)-containing a 67-polyQ repeat. Phage that specifically bound Htt were eluted and used to reinfect TG15 *E. coli*. Individual clones were tested again for Htt binding, and the nucleotide sequence of positive clones was determined by dideoxynucleotide chain-termination method. The nucleotide sequence of MW1, MW2, MW7 and MW8 scFVs are represented by SEQ ID NOs: 3, 4, 5 and 6, respectively.

2. Human MW9 scFv Antibody

For generation of hMW9 scFv, the cDNA for mutant huntingtin exon1 (HDx) fused to a His tag was expressed in *E.coli* and purified on nickel columns. The purified mutant protein was subjected to SDS-PAGE and transferred to nitrocellulose membranes. The nitrocellulose membranes were incubated with a human single-chain fragment variables (scFv) phage library encoding ~9×10$^{10}$ clones. Phage bound to HDx were selected and amplified by infection of susceptible *E.coli* for 5 rounds. Finally, amplified clones were selected with a recombinant GST-HDX in a solution-based assay. Individual clones were isolated, expressed and recombinant scFvs were tested for binding to His-HDx in vitro. Positive clones that bound in vitro were co-expressed with mutant HDx-1 in a tissue culture model of Huntington disease and results were evaluated for inhibition of cell death. hMW9 scFv expression inhibits aggregation and cell death induced by mutant HDx in this model.

B. Characterization of scFvs

1. Expression Analysis a. MW1, MW2, MW7 and MW8 scFvs

To test for scFv expression of the MW1, MW2, MW7 and MW8 anti-Htt antibodies, 293 cells were transfected with the Flag-tagged scFvs and cell lysates were analyzed by Western blotting and intracellular staining.

The reading frame for the scFvs were each subcloned into the mammalian plasmid pcDNA3.1 in frame with the Flag epitope for detection purposes (Chiang et al., Pept. Res., 6:62-64 (1993)). Selected clones were amplified and used to transfect 293 cells that were grown in DMEM supplemented with 10% heat inactivated bovine serum, 2 mM glutamine, 1 mM streptomycin and 100 international units of penicillin. Cells were grown in 6-well plates to about 70% confluence and transfected with a total of 2 µg of DNA by using lipofectamine, following the manufacturer's recommendations (Invitrogen). Expression of the scFvs were examined by Western blot analysis of the transfected cell extracts by using an anti-Flag Ab (Sigma).

Full-length proteins for MW1, MW2 and MW7 (FIG. 9A) scFvs were detected using anti-Flag Ab.

b. hMW9 scFv

Figure 10:
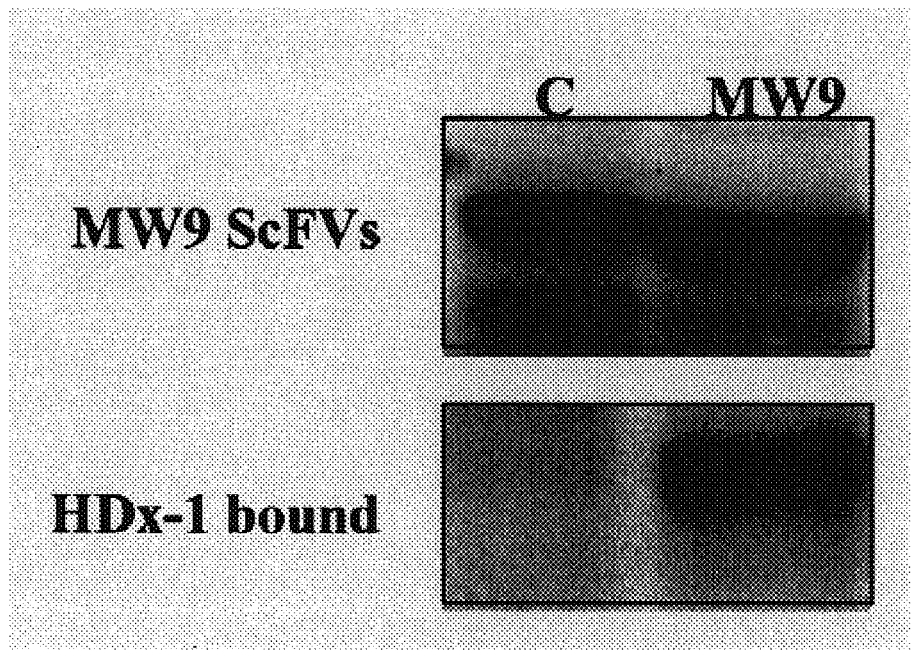
FIG. 10 shows expression of hMW9 scFv and a control scFv (C) as analyzed by in vitro transcription and translation of hMW9 scFv in the presence of $^{35}$S-methionine. The scFv was incubated with 5 μg of recombinant GST-HDx-1 bound to gluthathione beads and subsequent analysis of the scFv that bound to the glutathione beads by SDS-PAGE and autoradiography.

To test for scFv expression of the hMW9 anti-Htt antibodies, control and hMW9 scFvs were expressed by in vitro transcription and translation in the presence of $^{35}$S-methionine. Equal amounts of each were incubated with 5 µg of recombinant GST-HDx-1 bound to glutathione beads in a buffer containing mild detergent and glycerol. Following incubations for 3 hours at room temperature, the beads were washed 5 times in the buffer with mild detergent and glycerol. The scFvs that were bound to the beads were extracted and subjected to SDS-PAGE and autoradiography (FIG. 10).

2. Histological Analysis

For histological examination of 293 cells transfected with Flag-tagged scFvs, transfected cells were fixed in 4% paraformaldehyde for 30 minutes at 4° C., permeabilized in 70% methanol at −20° C. for 1 hour, and incubated with anti-Flag Ab (1:1000) for 2 hours. Cells expressing scFvs were detected by a goat anti-mouse Ab conjugated to Alexa 594 (Molecular Probes), and examined with a confocal microscope.

Figure 11:
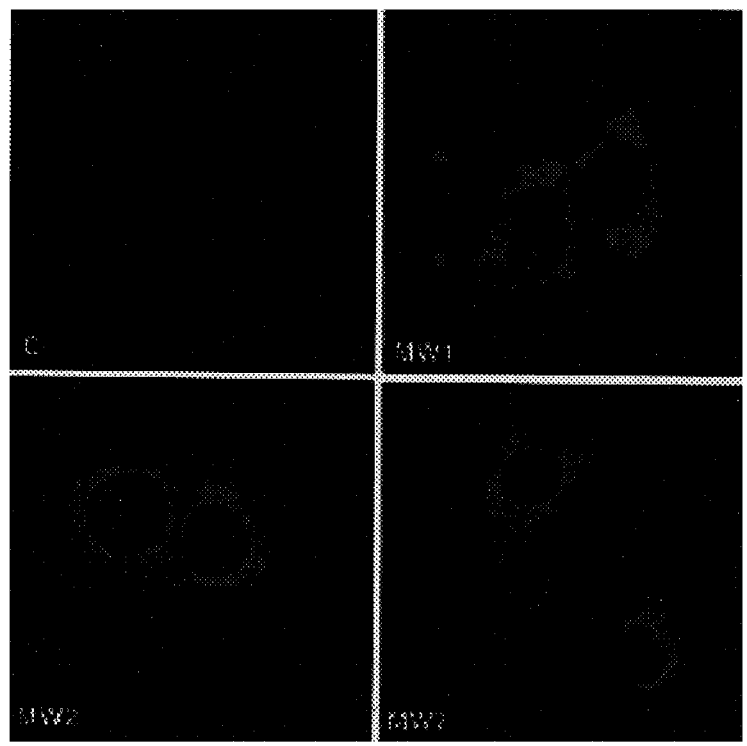
FIG. 11 shows immunofluorescence staining of 293 cells transfected with MW1, MW2 and MW7 scFvs or a control empty scFv vector (C) with anti-Flag antibodies two days after transfection and subsequent fixation.

Histological examination revealed that the MW1, MW2 and MW7 (FIG. 11) scFvs have a predominantly cytoplasmic distribution.

3. Cell Viability

Because other proteins besides Htt contain polyQ and polyP domains, it was of interest to test whether expression of the scFvs had an effect on cell viability.

To determine the effects of scFvs on cell viability, human 293 cells were cotransfected with each scFv and a plasmid encoding enhanced green fluorescent protein (EGFP; CLONTECH) as a transfection marker to readily detect which cells were transfected (Nucifora et al., Science, 291: 2423-2428 (2001)). Viable cells that expressed GFP were counted 4 days after transfection by using a fluorescence microscope.

After 4 days of growth, the mean cell counts from at least 30 microscope fields in six wells each revealed no significant differences between the control (112±6), and the scFvs for MW1 (97±3), MW2 (117±4), and MW7 (113±5). Accordingly, scFv expression did not affect cell growth or viability.

4. Interaction of Anti-Htt Antibody Fragments with Htt in Living Cells a. Coimmunoprecipitation To determine whether the scFvs interact with Htt in living cells, flag-tagged scFvs or flag-tagged IκBα, a control, were coexpressed in 293 cells with Htt exon 1 containing either 25 polyQ repeats (PQ25) or 103 polyQ repeats (PQ103), fused to EGFP and subjected to coimmunoprecipitation analysis. The scFvs and IκBα in Triton X-100 cell extracts were precipitated with anti-Flag Ab, and the precipitates were subjected to SDS-PAGE. The SDS-PAGE gels were analyzed for the presence of Htt exon 1 by Western blotting using anti-Flag Ab (FIG. 9A) and antibodies specific for the N-terminal 17 amino acids of exon 1 of the huntingtin protein (FIG. 9B).

Coimmunoprecipitation experiments were performed with 293 cell lysates cotransfected as described above. Briefly, cells were harvested 24 hours after transfection and lysed by sonication in buffer A (25 mM Hepes, pH 7.4/2.5 mM MgCl$_2$/50 mM NaCl/1 mM EDTA/1% Triton X-100). After clearing the lysates by centrifugation at 14,300 rpm (Eppendorf microcentrifuge) for 10 minutes at 4° C., 200 µg of each lysate was incubated at 4° C. with rocking for 2 hours with a 40-µl slurry of anti-Flag Ab coupled to protein A beads. The beads were then washed five times in buffer A by using centrifugation at 5,000 rpm, and the complexes were resolved on SDS-PAGE. For Western blotting, rabbit anti-HD1-17 (Mende-Mueller et al., J. Neurosci., 21:1830-1837 (2001)) and anti-Flag (1:1000; Sigma) were used as the primary Abs. Secondary antibodies conjugated to horseradish peroxidase (HRP) were used to detect the reactive protein bands by enhanced chemiluminescence (Santa Cruz Biotechnology). The SDS-PAGE gels were first probed with anti-flag antibodies for the presence of the scFvs and then stripped and reprobed with an antibody specific for the N-terminal 17 amino acids of exon 1 of the huntingtin protein for the presence of mutant PQ103 huntingtin about 80 kDa and mutant PQ25 huntingtin about 50 kDa.

Figure 9:
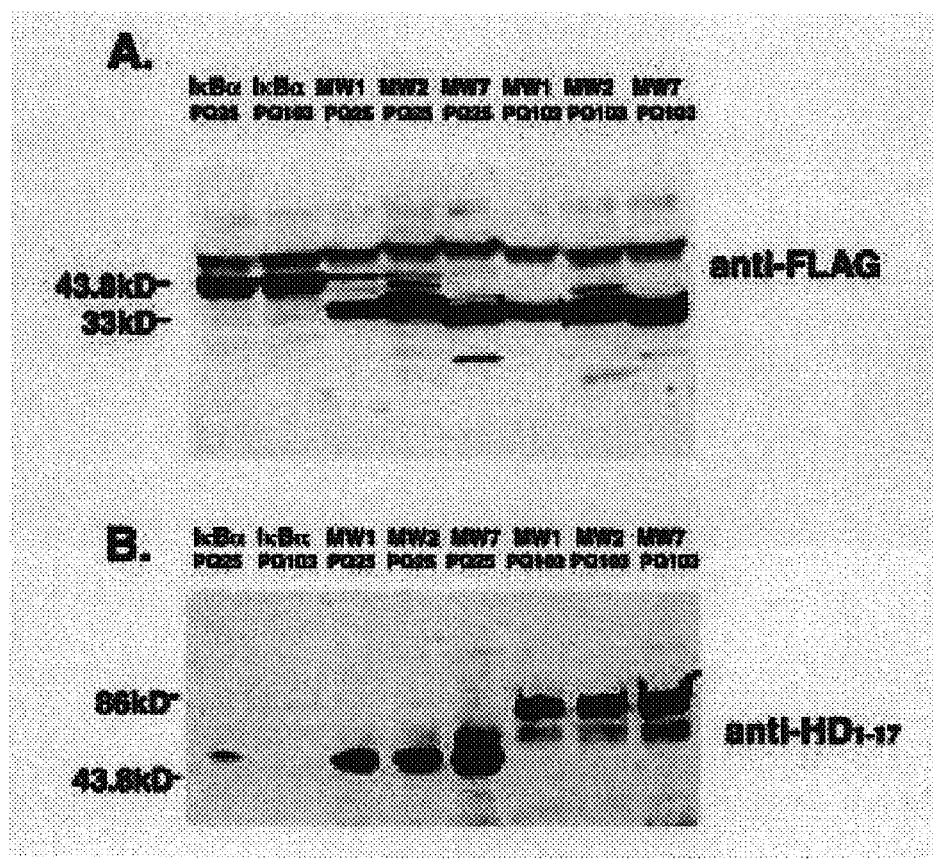
FIG. 9 shows coimmunoprecipitation of expressed MW scFv proteins from lysates of 293 cells cotransfected with Htt exon 1-EGFP, either 25-residue polyQ (PQ25) or 103-residue polyQ (PQ103), and a Flag-scFv or Flag-IκBα.

As shown in FIG. 9A, similar amounts of each of the MW1, MW2 and MW7 scFvs, which migrate with a molecular mass of about 35 kDa and IκBα which migrates with a molecular mass of about 43 kDa were precipitated with the anti-Flag Ab (FIG. 9A), and mutant Htt exon 1 (PQ103) coimmunoprecipitates with each scFv (FIG. 9B; 86-kDa bands). Similar results were obtained when Htt exon 1 with a 25-Q stretch (PQ25) was used for transfection (FIG. 9B; 50 kDa bands). As a negative control, in cells expressing Flag-tagged IκBα, IκBα was precipitated from the extract by the anti-Flag Ab (FIG. 9A; 44-kDa band), but Htt was not coprecipitated (FIG. 9B). The bands below 30 kDa in FIG. 9B likely represented nonspecific staining of the precipitating Ab.

5 Colocalization

To confirm binding of the scFvs to mutant huntingtin protein and to localize the sites of interaction within cells, we used confocal microscopy to examine 293 cells cotransfected with mutant exon 1 of the huntingtin protein having 103 Q repeats and fused to EGFP (103-Q Htt-EGFP) and each anti-Htt scFv.

For colocalization experiments, the scFvs and 103-Q Htt-EGFP, obtained from the Cure Huntington Disease Initiative Resource Bank (Univ. of California, Los Angeles; Steffan et al., Proc. Natl. Acad. Sci. USA, 97:6763-6768 (2000)), were cotransfected in 293 cells grown on coverslips. 24 hours after transfection, cells were fixed, stained, and examined as described above. Depending on the experiment, 50-70% of the cells expressed EGFP.

Although the MW1, MW2 and MW7 (FIG. 11) scFvs and MW8 scFvs were distributed throughout the cytoplasm in the absence of Htt, when contransfected with 103-Q Htt-EGFP, the MW1, MW2 and MW7 (FIG. 13) and MW8 (FIG. 14) scFvs were concentrated in the perinuclear region and colocalized with 103-Q Htt-EGFP.

6. Effects of Anti-Htt Antibody Fragments on Htt-Induced Cell Death

To evaluate the effect of anti-Htt scFvs on the toxic effects of mutant Htt, we examined by terminal deoxynucleotidyl-transferase-mediated dUTP nick end labeling (TUNEL) staining of 293 cells cotransfected with 103-Q Htt-EGFP and each scFv.

Two days after cotransfection, 293 cells were fixed as described above and washed three times in PBS. The TUNEL reaction consisted of 25 units of terminal deoxynucleotidyltransferase and 1 mM dUTP conjugated to tetramethylrhodamine (Roche Molecular Biochemicals) in 1× buffer/2.5 mM $CoCl_2$ in a final volume of 50 µl (according to manufacturer's instructions). Coverslips with fixed cells were laid over the reaction mixture and incubated at 37° C. in a humidified incubator. Samples were washed four times with PBS, mounted on microscope slides, and examined by confocal microscopy. TUNEL-positive cells that were expressing mutant Htt exon 1 were counted from at least 16 independent microscope fields with a ×20 objective lens in four separate experiments. The data were analyzed by using EXCEL software to determine the standard deviation and the P value (t test).

Figure 13:
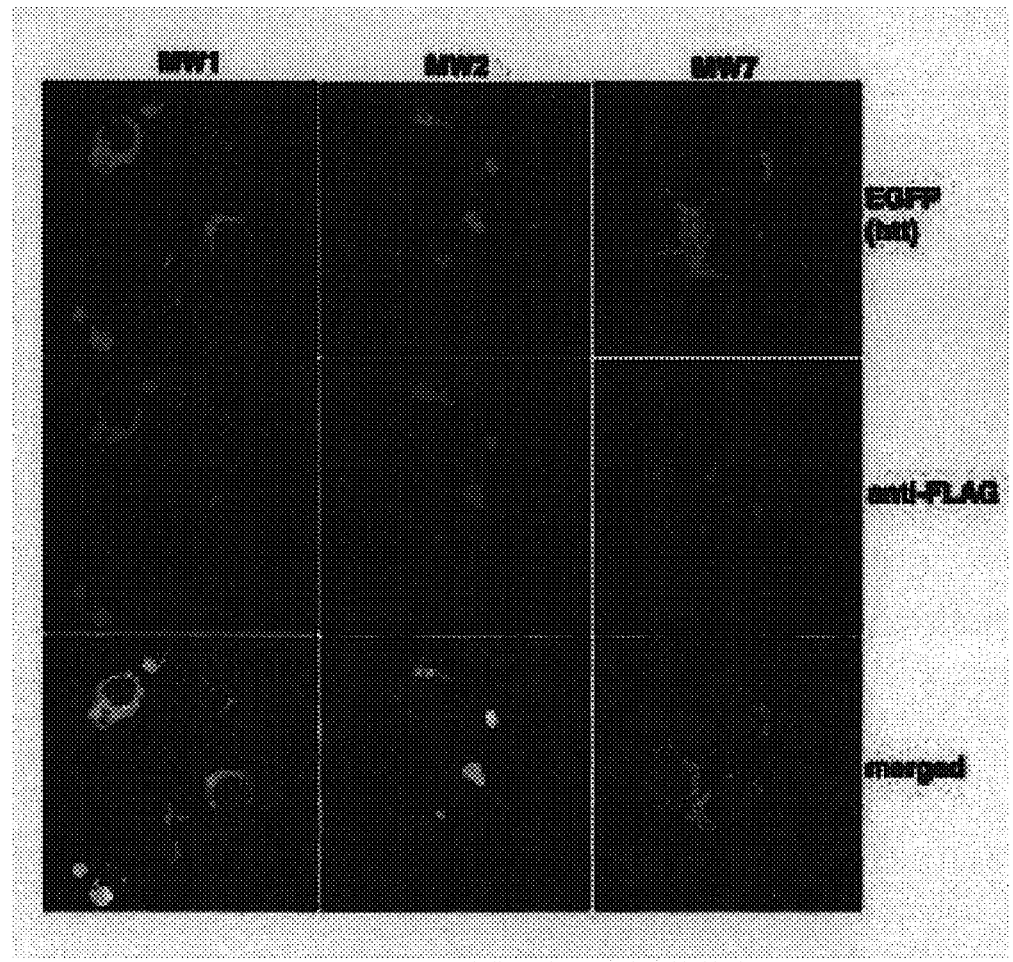
FIG. 13 shows colocalization of MW1, MW2 or MW7 scFv with mutant Htt in 293 cells cotransfected with mutant Htt fused to EGFP tag and scFv tagged with a Flag tag.
Figure 14:
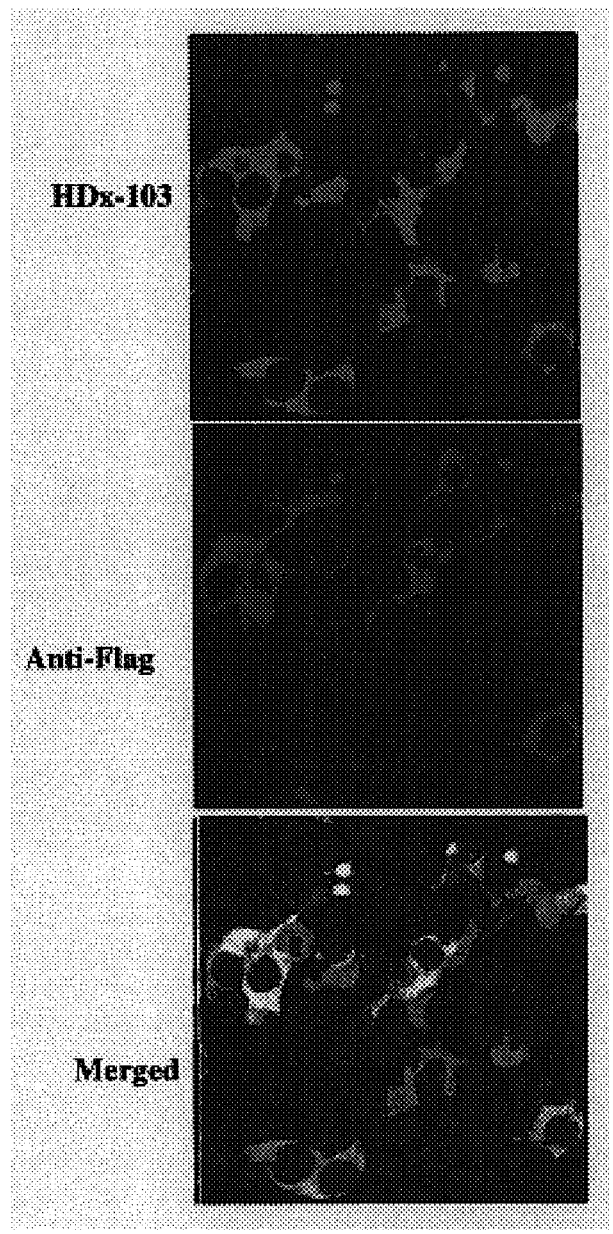
FIG. 14 shows colocalization of MW8 scFv with mutant Htt in 293 cells cotransfected with mutant Htt fused to EGFP tag and scFv tagged with a Flag tag.
Figure 15:
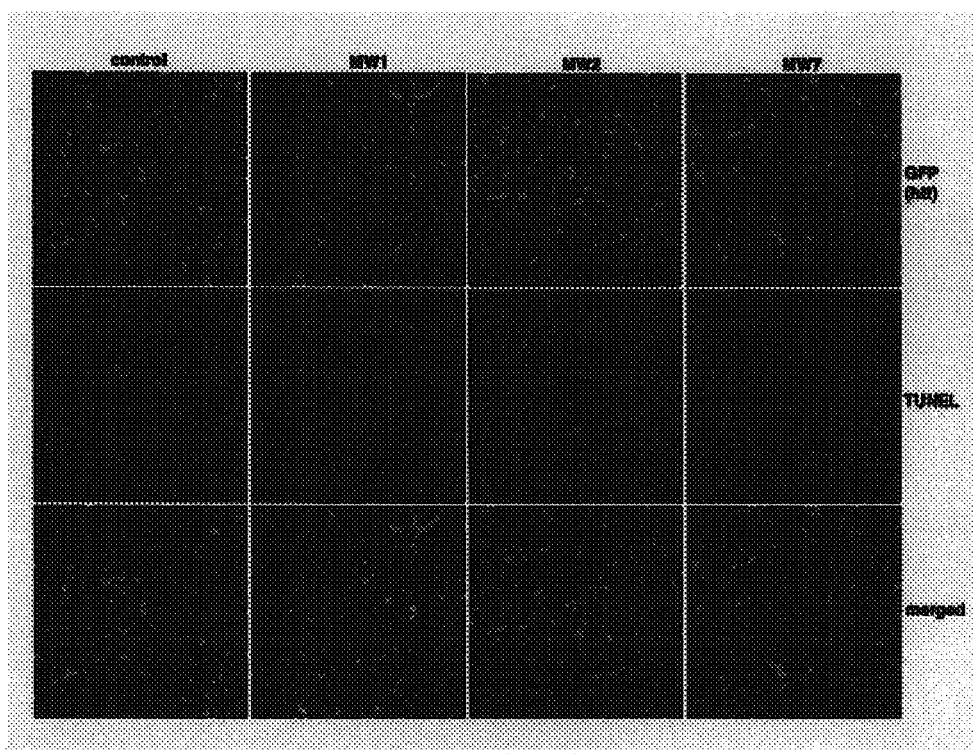
FIG. 15 shows inhibition of Htt-induced cell death in 293 cells with MW7 scFv and enhancement of Htt-induced cell death in 293 cells with MW1 or MW2 scFvs. 293 cells were transfected with Htt exon 1-EGFP and an empty vector (control) or one of the anti-huntingtin scFvs, MW1, MW2 or MW7 tagged with a Flag tag. The transfected cells were visualized by GFP fluorescence, and dying cells by TUNEL staining. The presence of MW7 scFv decreases the number of TUNEL+cells.

Cells expressing 103-Q Htt-EGFP along with an empty scFv vector displayed significant TUNEL staining, and apoptotic bodies were observed starting about 12 hours after transfection (FIG. 13, control column). TUNEL staining was even more dramatic in the presence of MW1 or MW2 scFv and mutant Htt (FIG. 15). MW1 or MW2 scFv binding to the polyQ domain accentuated the toxicity of mutant Htt.

Expression of MW7 scFv (FIG. 15) or MW8 scFv (FIG. 16) inhibited the toxicity of mutant Htt. These experiments were done under the same conditions as in FIG. 9A, which demonstrated equivalent expression of MW1, MW2 and MW7 scFvs in the cells.

Figure 16:
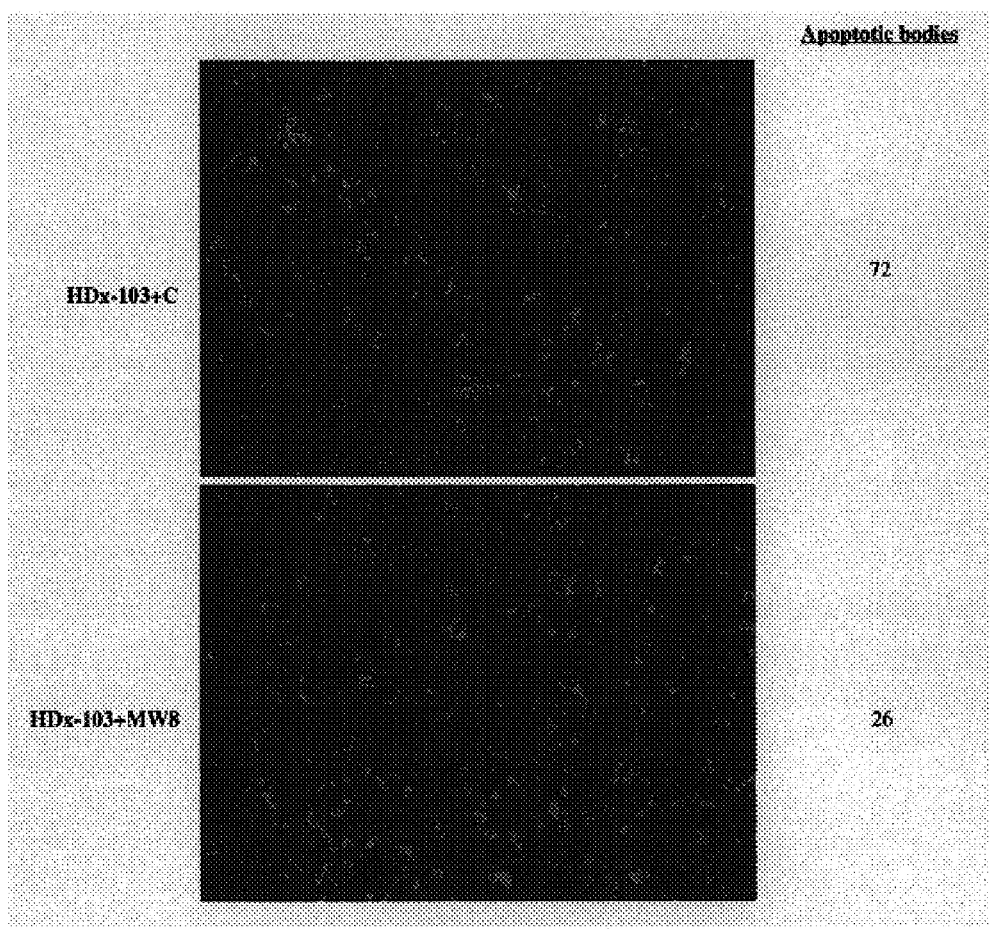
FIG. 16 shows inhibition of Htt-induced cell death in 293 cells with MW8 scFv. 293 cells were transfected with Htt exon 1-EGFP and an empty vector (control) or MW8 anti-huntingtin scFv, tagged with a Flag tag. The transfected cells were visualized by GFP fluorescence, and dying cells by TUNEL staining. The presence of MW8 scFv decreases the number of TUNEL+cells.
Figure 17:
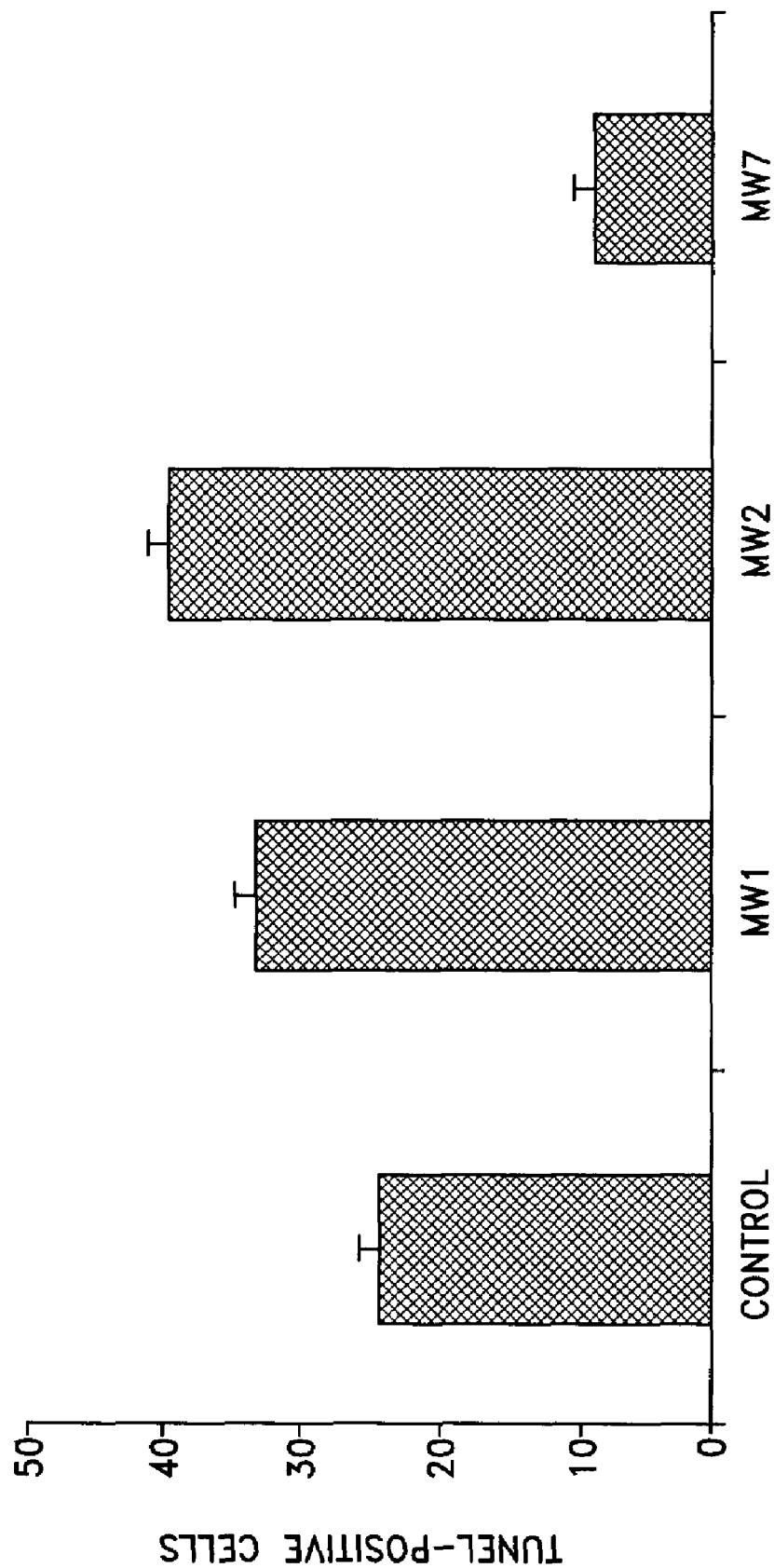
FIG. 17 shows a chart representing quantitation of the effects of the expression of anti-huntingtin antibodies, MW1, MW2 and MW7 on mutant Htt toxicity. MW1 and MW2 exacerbated Htt-induced cell death while MW7 inhibited Htt toxicity.

To quantify the effects of scFv expression on mutant Htt toxicity, we counted TUNEL+ cells. The increase in mutant Htt-induced TUNEL staining in the presence of MW1 and −2 scFvs is 38% and 67%, respectively (P<0.05) (FIG. 17). In contrast, the number of TUNEL+ cells in the presence of MW7 scFv is reduced to 33% of the control (P<0.05) FIG. 15), and the number of TUNEL+ cells in the presence of MW8 scFv is reduced from 72 apoptotic bodies to 26 apoptotic bodies (FIG. 16). Thus, although the anti-polyQ mAbs MW1 and MW2 scFvs accentuate the toxicity of mutant Htt, expression of the anti-polyP mAb MW7 and MW8 scFvs inhibits the toxicity of mutant Htt.

Figure 12:
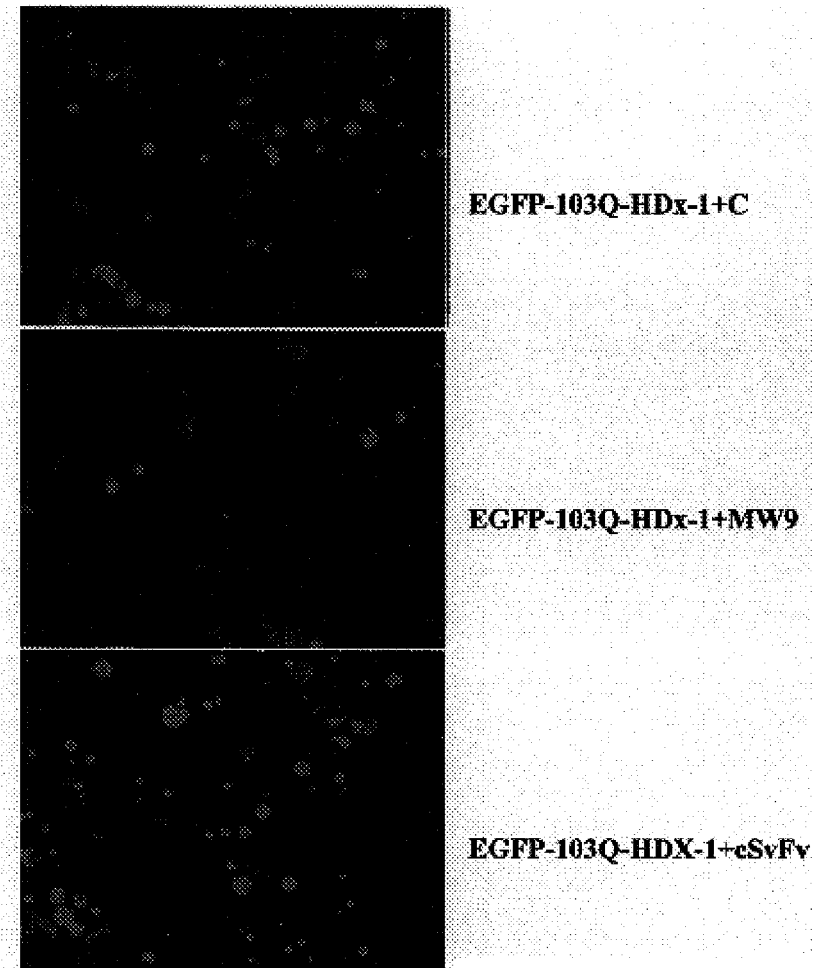
FIG. 12 shows the effects of the expression of hMW9 scFv, empty plasmid (C) or control plasmid (cscFv) and HDx-1, containing 103 polyQ and fused to GFP in human 293 cells as analyzed by fluorescence microscopy.

To determine the effects of hMW9 scFv on mutant Htt cell toxicity, human 293 cells were cotransfected with the 103-Q Htt-EGFP and hMW9 or as controls, an empty plasmid or a control scFv that does not bind to exon 1 of the huntingtin protein (HDx-1) by lipofectamine. 103-Q Htt-EGFP, was cotransfected with an empty plasmid (FIG. 12; EGFP-103Q-HDx-1+C), hMW9 (FIG. 12; EGFP-103Q-HDx-1+MW9) or cscFv, a control that does not bind to HDx-1 (FIG. 12; EGFP-103Q-HDx-1+cscFv). Two days post-transfection cells were examined by a fluorescent microscope. Cells remained intact in the presence of hMW9 (middle panel) when compared to the presence of a control that does not bind to HDx-1 (bottom panel). Without hMW9, mutant Htt results in cell toxicity and the presence of apoptotic bodies (FIG. 12, top panel). In the presence of hMW9, cells transfected with mutant Htt are healthy and have less apoptotic bodies (FIG. 12, middle panel).

7. Effects of Anti-Htt Antibody Fragments on Aggregation of Mutant Htt

To evaluate the effects of scFv expression on mutant Htt aggregation in 293 cells, Htt aggregation was evaluated biochemically by examining the amount of Htt that precipitated from cell lysates by centrifugation at 150,000×g for 30 min.

For aggregation studies, 293 cells were cotransfected with mutant Htt exon 1 and an scFv were harvested 48 hours after transfection. Cells were lysed by sonication in buffer A. Lysates were centrifuged at 150,000×g in an SW55 rotor (Beckman Instruments, Fullerton, Calif.) for 30 minutes (Nucifora et al., Science, 291:2423-2428 (2001)). Pellets were dissolved in sample buffer containing 2% SDS, boiled and subjected to SDS-PAGE, and transferred to nitrocellulose membranes for immunoblotting analysis. Aggregates were detected with anti-HD1-17 polyclonal antibody (Mende-Mueller et al., J. Neurosci., 21:1830-1837 (2001)).

Figure 18:
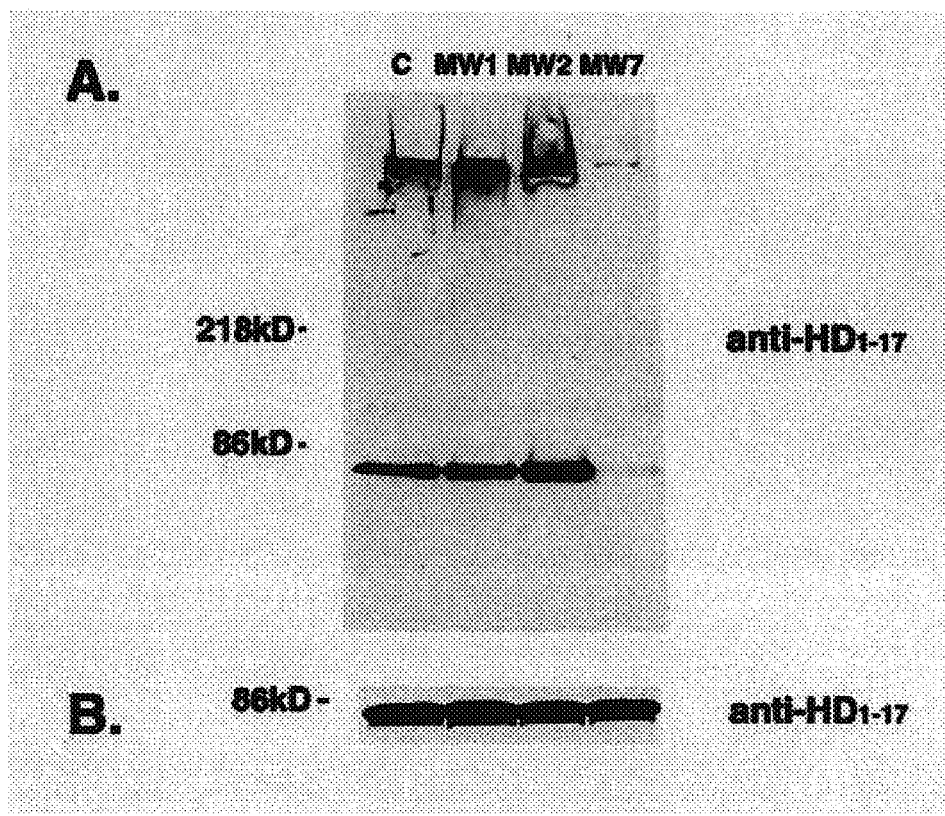
FIGS. 18A-18B show reduction of aggregation of mutant huntingtin protein in 293 cells as analyzed by Western blotting. Lysates of 293 cells transfected with mutant Htt and an scFv, MW1, MW2 or MW7, were subjected to high-speed centrifugation and were analyzed by Western blotting with anti-HD$_{1-17}$ antibodies. The Htt in the pellet that can be solubilized by SDS treatment is about 80 kDa, whereas the Htt that cannot be solubilized does not enter the gel and is visualized as a band at the top of the gel (FIG. 18A).

The pellets contained aggregated Htt (or Htt that is bound to large structures) that can be solubilized by SDS treatment (FIG. 18A, 80-kDa bands), as well as Htt that remained insoluble after boiling in SDS and cannot enter the gel (FIG. 18A, top of gel). Both such species of pelleted Htt were detected in extracts of cells transfected with mutant Htt exon 1 alone (FIG. 18A). Aggregation increased when mutant Htt exon 1 was coexpressed with MW1 scFv or MW2 scFv. Very little aggregated Htt was found in the presence of MW7, MW8 or hMW9 scFv. Scanning the bands at the top of the gel in FIG. 18 yielded values in arbitrary units of 68.8 for MW1, 54.3 for MW2, 0.2 for MW7, and 48.8 for no scFv.

Accordingly, coexpression of MW7 scFv interfered with aggregation of mutant Htt exon 1, and there was a qualitative correlation between the effects of the scFvs on Htt aggregation and toxicity. The expression of MW7 did not cause a depletion in the level of soluble Htt (FIG. 18B).

Coexpression of hMW9 also interfered with aggregation of mutant Htt exon 1.

What is claimed is:

1. An isolated monoclonal antibody that specifically binds an epitope within a polyproline region of the huntingtin protein comprising greater than 5 consecutive proline residues;

wherein said antibody is capable of inhibiting aggregation of the huntingtin protein;

wherein said monoclonal antibody is a single-chain variant fragment encoded by a nucleotide sequence comprising SEQ ID NO: 5.

* * * * *

SEQUENCE LISTING

<160> NUMBER OF SEQ ID NOS: 6

<210> SEQ ID NO 1
<211> LENGTH: 91
<212> TYPE: PRT
<213> ORGANISM: Homo sapiens

<400> SEQUENCE: 1

Met Ala Thr Leu Glu Lys Leu Met Lys Ala Phe Glu Ser Leu Lys Ser
 1               5                  10                  15

Phe Gln Gln Gln Gln Gln Gln Gln Gln Gln Gln Gln Gln Gln Gln
            20                  25                  30

Gln Gln Gln Gln Gln Gln Gln Pro Pro Pro Pro Pro Pro Pro
        35                  40                  45

Pro Pro Pro Gln Leu Pro Gln Pro Pro Pro Gln Ala Gln Pro Leu Leu
 50                  55                  60

Pro Gln Pro Gln Pro Pro Pro Pro Pro Pro Pro Pro Gly Pro
 65                  70                  75                  80

Ala Val Ala Glu Glu Pro Leu His Arg Pro Lys
            85                  90

<210> SEQ ID NO 2
<211> LENGTH: 8
<212> TYPE: PRT
<213> ORGANISM: Homo sapiens

<400> SEQUENCE: 2

Ala Glu Glu Pro Leu His Arg Pro
 1               5

<210> SEQ ID NO 3
<211> LENGTH: 746
<212> TYPE: DNA
<213> ORGANISM: Homo sapiens

<400> SEQUENCE: 3
atggcccagg tcaaactgca ggagtctggg ggaggcttag tgcagcctgg agggtccctg        60
aaactctcct gtcagcctc tggattcact ttcagagact attatatgta ttgggttcgc       120
cagactccag agaagaggct ggagtgggtc gcattcatta gtaatggtgg tggtagcacc       180
tattatccag acactgtaaa gggccgattc accatctcca gagacaatgc caagaacacc       240
ctgtacctgc aaatgagccg tctgaagtct gaggacacag ccatgtatta ctgtgcaaga       300 gggagggct acgtatggtt tgcttactgg ggccaaggga ccacggtcac cgtcttctca       360
ggtggaggcg gttcaggcgg aggtggctct ggcggtggcg gatcggacat tgtgctaacc       420
cagtctccag cttccttagc tgtatctctg gggcagaggg ccaccatctc atacagggcc       480
agcaaaagtg tcagtacatc tggctatagt tatatgcact ggaaccaaca gaaaccagga       540
cagccaccca gactcctcat ctatcttgta tccaacctag aatctggggt ccctgccagg       600
ttcagtggca gtgggtctgg gacagacttc accctcaaca tccatcctgt ggaggaggag       660
gatgctgcaa cctattactg tcagcacatt agggagctta cacgttcgga ggaggcacca       720
agctggaaat caaacgggcg gccgca                                            746

<210> SEQ ID NO 4
<211> LENGTH: 761
<212> TYPE: DNA

<213> ORGANISM: Homo sapiens

<400> SEQUENCE: 4

| | | | | | |
|---|---|---|---|---|---|
| atggcccagg | tgaaactgca | ggagtcagga | cctgagctga | agaagcctgg | agagacagtc | 60 |
| aagatctcct | gcaaggcttc | tgggtatacc | ttcacaaact | atggaatgaa | ctgggtgaag | 120 |
| caggctccag | gaaagggttt | aaagtggatg | gctggataa | acacctacac | tggagagcca | 180 |
| acatatgctg | atgactccaa | gggacggttt | gccttctctt | tggaaacctc | tgccagcact | 240 |
| gcctatttgc | agatcaacaa | cctcaaaaat | gaggacatgg | ctacatattt | ctgtgcaaga | 300 |
| aggggattac | tgtttgctta | ctggggccaa | ggaccacgg | tcaccgtctc | tcaggtgga | 360 |
| ggcggttcag | gcggaggtgg | ctctggcggt | ggcggaggtg | gctctggcgg | tggcggatcg | 420 |
| gacatcgagc | tcactcagtc | tccaacttcc | ttagctgtat | ctctggggca | gagggccacc | 480 |
| atctcataca | gggccagcaa | aagtgtcagt | acatctggct | atagttatat | gcactggaac | 540 |
| caacagaaac | caggacagcc | acccagactc | ctcatctatc | ttgtatccaa | cctagaatct | 600 |
| ggggtccctg | ccaggttcag | tggcagtggg | tctgggacag | acttcaccct | caacatccat | 660 |
| cctgtggagg | aggaggatgc | tgcaacctat | tactgtcagc | acattaggga | gcttacacgt | 720 |
| tcggaggggg | gacaaagttg | gaaataaaac | gggcggccgc | a | | 761 |

<210> SEQ ID NO 5
<211> LENGTH: 826
<212> TYPE: DNA
<213> ORGANISM: Homo sapiens

<400> SEQUENCE: 5

| | | | | | |
|---|---|---|---|---|---|
| atggactaca | aggacgacga | tgacaaggtg | gcccaggtca | agctgcagga | gtctggagga | 60 |
| ggcttggtgc | aacctggagg | atccatgaaa | ctctcttgtg | ctgcctctgg | attcactttt | 120 |
| agtgacgcct | ggatggactg | ggtccgccag | tctccagaga | aggggctgag | tggggttgct | 180 |
| gaaattagaa | gcaaagctaa | taatcatgca | acatactatg | ctgagtctgt | gaaagggagg | 240 |
| ttcaccatct | caagagatga | ttccaaaagt | agtgtctacc | tgcaaatgaa | cagcttaaga | 300 |
| gctgaagaca | ctggcattta | ttactgtatc | tatgcggggt | ttgcttactg | gggccaaggg | 360 |
| accacggtca | ccgtctcctc | aggtggaggc | ggttcaggcg | gaggtggctc | tggcggtggc | 420 |
| ggatcggaca | tcgagctcac | tcagtctcca | tcctccctgg | ctatgtcagt | aggacagaag | 480 |
| gtcactatga | gctgcaagtc | cagtcagagc | cttttaaata | gtagcaatca | aaagaactat | 540 |
| ttggcctggt | accagcagaa | accaggacag | tctcctaaac | ttctggtata | ctttgcatcc | 600 |
| actagggaat | ctggagtccc | tgatcgcttc | ataggcagtg | gatctgggac | agatttcact | 660 |
| cttaccatca | gcagtgtgca | ggctgaagac | ctggcagatt | acttctgtca | gcaacattat | 720 |
| agcactccgt | ggacgttcgg | tggaggcacc | aagctggaaa | tcaaacgggg | acaaagttgg | 780 |
| aaataaaacg | tgggggacc | aagctggaaa | taaaacgggc | ggccgc | | 826 |

<210> SEQ ID NO 6
<211> LENGTH: 729
<212> TYPE: DNA
<213> ORGANISM: Homo sapiens

<400> SEQUENCE: 6

| | | | | | |
|---|---|---|---|---|---|
| atggcccagg | tgcagctgca | ggagtcaggg | ggaggcttag | tgaagcctgg | agggtccctg | 60 |
| aaactctcct | gtcagcctc | tggattcact | ttcagtgact | attacatgta | ttgggttcgc | 120 |
| cagactccgg | aaaagaggct | ggagtgggtc | gcaaccatta | gtgatggtgg | tagttacacc | 180 |

```
tactatccag acaatatgaa ggggcgattc accatctcca gagacaatgc caagaacaac    240
ctgtacctgc aaatgagcag tctgaagtct gaggatacag ccatgtattt ttgtgcaaga    300
gatctgggga aatggggcca aggcaccacg gtcaccgtct cctcaggtgg aggcggttca    360
ggcggaggtg gctctggcgg tggcggatcg gacatcgagc tcactcagtc tccaacttcc    420
ttagctgtat ctctgggca gagggccacc atctcataca gggccagcaa aagtgtcagt     480
acatctggct atagttatat gcactggaac caacagaaac caggacagcc acccagactc    540
ctcatctatc ttgtatccaa cctagaatct ggggtccctg ccaggttcag tggcagtggg    600
tctgggacag acttcaccct caacatccat cctgtggagg aggaggatgc tgcaacctat    660
tactgtcagc acattaggga gcttacacgt tcggagggg accaagctgg aaataaaacg     720
ggcggccgc                                                           729
```